(12) United States Patent
Ralph et al.

(10) Patent No.: US 7,927,339 B2
(45) Date of Patent: Apr. 19, 2011

(54) SYSTEMS AND METHODS FOR REDUCING FRACTURED BONE USING A FRACTURE REDUCTION CANNULA WITH A SIDE DISCHARGE PORT

(75) Inventors: Christopher R. Ralph, Mountain View, CA (US); Richard W. Layne, Sunnyvale, CA (US); Paul M. Sand, San Carlos, CA (US); Robert M. Scribner, Niwot, CO (US); Mark A. Reiley, Piedmont, CA (US)

(73) Assignee: Kyphon SARL, Neuchatel (CH)

( * ) Notice: Subject to any disclaimer, the term of this patent is extended or adjusted under 35 U.S.C. 154(b) by 544 days.

(21) Appl. No.: 11/789,639

(22) Filed: Apr. 25, 2007

(65) Prior Publication Data

US 2008/0065020 A1 Mar. 13, 2008

Related U.S. Application Data

(60) Continuation of application No. 11/637,396, filed on Dec. 12, 2006, now abandoned, which is a division of application No. 10/001,937, filed on Oct. 25, 2001, now Pat. No. 7,153,306, which is a continuation-in-part of application No. 09/804,107, filed on Mar. 12, 2001, now Pat. No. 6,613,054, which is a division of application No. 09/134,323, filed on Aug. 14, 1998, now Pat. No. 6,241,734.

(60) Provisional application No. 60/243,194, filed on Oct. 25, 2000.

(51) Int. Cl.
*A61B 17/58* (2006.01)
*A61F 2/00* (2006.01)

(52) U.S. Cl. .......................................... 606/92

(58) Field of Classification Search ................ 606/86 R, 606/92–94, 96–98, 108, 191–194, 198; 604/104, 604/164.01, 164.03, 164.04, 164.11, 166.01, 604/264
See application file for complete search history.

(56) References Cited

U.S. PATENT DOCUMENTS

| | | | |
|---|---|---|---|
| 4,005,527 | A | 2/1977 | Wilson et al. |
| 4,083,369 | A | 4/1978 | Sinnreich |
| 4,205,683 | A | 6/1980 | O'Neill |
| 4,313,434 | A | 2/1982 | Segal |
| 4,327,736 | A | 5/1982 | Inoue |
| 4,357,716 | A | 11/1982 | Brown |
| 4,494,535 | A | 1/1985 | Haig |
| 4,842,585 | A | 6/1989 | Witt |

(Continued)

FOREIGN PATENT DOCUMENTS

DE 8800197 U1 6/1988

(Continued)

*Primary Examiner* — Anu Ramana
(74) *Attorney, Agent, or Firm* — Haynes and Boone, LLP

(57) ABSTRACT

An elongated shaft is sized and configured to establish an access path to bone having an interior volume occupied, at least in part, by cancellous bone. The elongated shaft includes a generally closed distal end portion and a side opening spaced from the closed distal end. A first tool is sized and configured to be selectively inserted into the shaft and selectively removed from the shaft. The tool includes a region that, when the first tool is inserted into the shaft, is capable of being aligned with and advanced through the side opening to project outside the side opening and contact cancellous bone. A second tool is sized and configured, upon removal of the first tool from the shaft, to introduce into the shaft a bone filling material for discharge through the side opening into the cancellous bone contacted by the first tool.

11 Claims, 18 Drawing Sheets

U.S. PATENT DOCUMENTS

| | | | |
|---|---|---|---|
| 4,919,153 | A | 4/1990 | Chin |
| 4,969,888 | A | 11/1990 | Scholten et al. |
| 5,013,318 | A | 5/1991 | Spranza, III |
| 5,102,413 | A | 4/1992 | Poddar |
| 5,108,404 | A | 4/1992 | Scholten et al. |
| 5,116,305 | A | 5/1992 | Milder et al. |
| 5,171,248 | A | 12/1992 | Ellis |
| 5,176,683 | A | 1/1993 | Kimsey et al. |
| 5,254,091 | A | 10/1993 | Aliahmad |
| 5,359,995 | A | 11/1994 | Sewell, Jr. |
| 5,380,290 | A | 1/1995 | Makower et al. |
| 5,423,850 | A | 6/1995 | Berger |
| 5,439,447 | A | 8/1995 | Miraki |
| 5,467,786 | A | 11/1995 | Allen et al. |
| 5,468,245 | A | 11/1995 | Vargas, III |
| 5,480,400 | A | 1/1996 | Berger |
| 5,484,442 | A | 1/1996 | Melker et al. |
| 5,514,137 | A | 5/1996 | Coutts |
| 5,545,136 | A | 8/1996 | Berger |
| 5,601,559 | A | 2/1997 | Melker et al. |
| 5,658,310 | A | 8/1997 | Berger |
| 5,741,261 | A | 4/1998 | Moskovitz et al. |
| 5,792,044 | A | 8/1998 | Foley et al. |
| 5,807,329 | A | 9/1998 | Gelman |
| 5,817,074 | A | 10/1998 | Racz |
| 5,824,087 | A | 10/1998 | Aspden et al. |
| 5,827,289 | A | 10/1998 | Reiley et al. |
| 5,849,014 | A | 12/1998 | Mastrorio et al. |
| 5,865,728 | A | 2/1999 | Moll et al. |
| 5,928,162 | A | 7/1999 | Giurtino et al. |
| 5,961,499 | A | 10/1999 | Bonutti et al. |
| 5,972,015 | A | 10/1999 | Scribner et al. |
| 5,989,260 | A | 11/1999 | Yao |
| 5,997,581 | A | 12/1999 | Khalili |
| 6,036,682 | A | 3/2000 | Lange et al. |
| 6,036,711 | A | 3/2000 | Mozdzierz et al. |
| 6,048,346 | A | 4/2000 | Reiley et al. |
| 6,066,122 | A | 5/2000 | Fisher |
| 6,066,154 | A | 5/2000 | Reiley et al. |
| 6,127,597 | A | 10/2000 | Beyar et al. |
| 6,241,734 | B1 | 6/2001 | Scribner et al. |
| 6,248,110 | B1 | 6/2001 | Reiley et al. |
| 6,280,456 | B1 | 8/2001 | Scribner et al. |
| 6,423,083 | B2 | 7/2002 | Reiley et al. |
| 6,440,138 | B1 | 8/2002 | Reiley et al. |
| 6,468,279 | B1 | 10/2002 | Reo |
| 6,488,653 | B1 | 12/2002 | Lombardo |
| 6,582,446 | B1 | 6/2003 | Marchosky |
| 6,607,544 | B1 | 8/2003 | Boucher et al. |
| 6,726,691 | B2 | 4/2004 | Osorio et al. |
| 2002/0010472 | A1 | 1/2002 | Kuslich et al. |
| 2002/0032447 | A1 | 3/2002 | Weikel et al. |
| 2002/0099385 | A1 | 7/2002 | Ralph et al. |
| 2002/0173796 | A1 | 11/2002 | Cragg |
| 2003/0050702 | A1 | 3/2003 | Berger |
| 2003/0130664 | A1 | 7/2003 | Boucher et al. |

FOREIGN PATENT DOCUMENTS

| | | |
|---|---|---|
| DE | 3922044 A1 | 7/1989 |
| JP | 8038618 | 2/1996 |
| WO | 90-04364 A1 | 5/1990 |
| WO | WO 97/28840 | 8/1997 |
| WO | 9856301 | 12/1998 |
| WO | WO 98/56301 | 12/1998 |
| WO | WO 99/02214 | 1/1999 |
| WO | WO 99/37212 | 7/1999 |
| WO | WO 99/62416 | 12/1999 |
| WO | WO 00/09024 | 2/2000 |
| WO | 00-54705 A1 | 9/2000 |
| WO | WO 01/76492 | 10/2001 |
| WO | WO 01/76514 | 10/2001 |

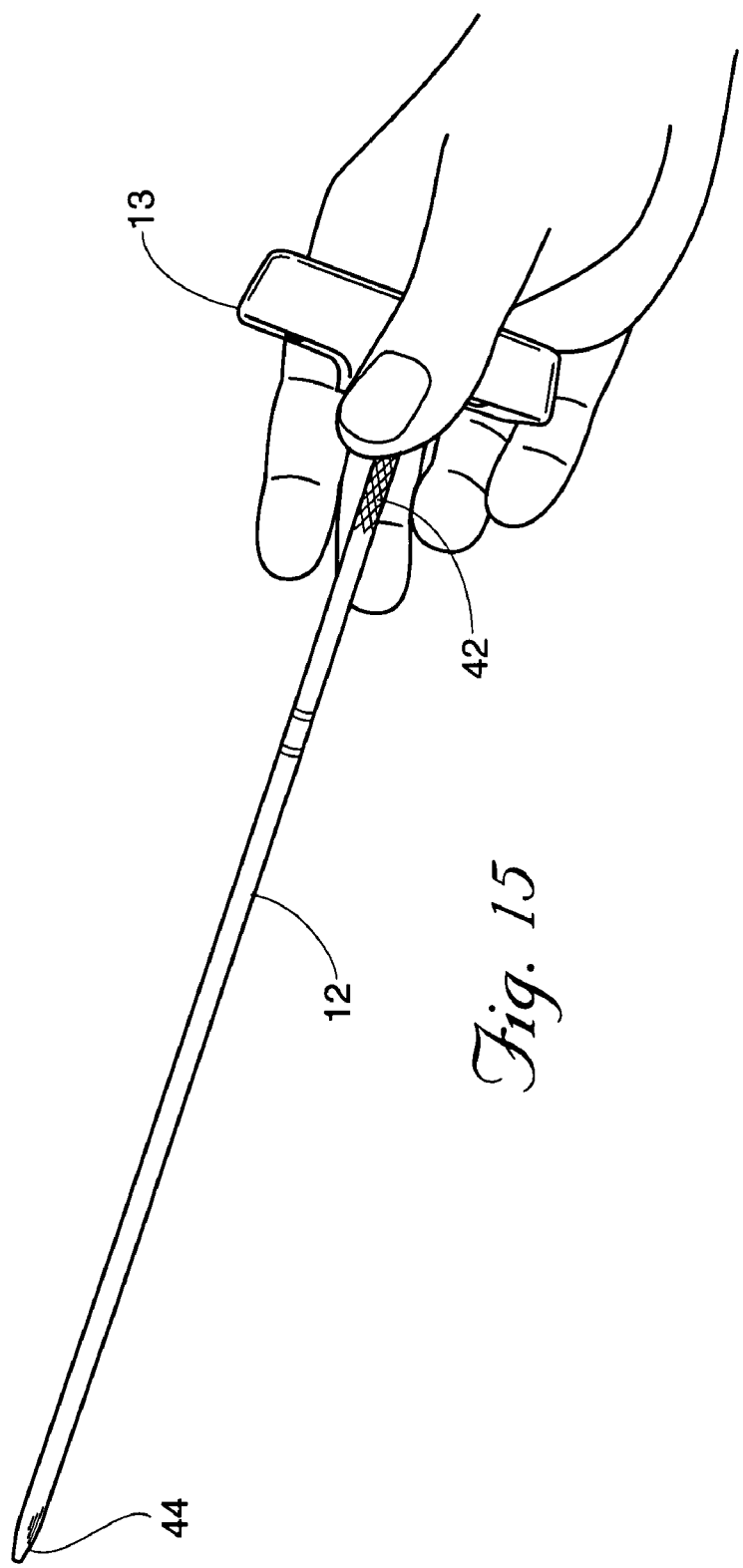

SYSTEMS AND METHODS FOR REDUCING FRACTURED BONE USING A FRACTURE REDUCTION CANNULA WITH A SIDE DISCHARGE PORT

RELATED APPLICATIONS

This application is a continuation of co-pending U.S. patent application Ser. No. 11/637,396 filed 1 Dec. 2006 and entitled "Systems and Methods for Reducing Fractured Bone Using a Fracture Reduction Cannula," which is a divisional of U.S. patent application Ser. No. 10/001,937 filed 25 Oct. 2001 (now U.S. Pat. No. 7,153,306, which claims the benefit of Provisional U.S. Patent Application Ser. No. 60/243,194 filed 25 Oct. 2000 and which is also a Continuation-in-part of U.S. patent application Ser. No. 09/804,107 filed 12 Mar. 2001 (now U.S. Pat. No. 6,613,054), which is a divisional of U.S. patent application Ser. No. 09/134,323 filed 14 Aug. 1998 (now U.S. Pat. No. 6,241,734).

FIELD OF THE INVENTION

This invention relates to the treatment of bone conditions of the human and other animal body systems and, more particularly, to systems and methods for correcting such conditions.

BACKGROUND OF THE INVENTION

Bone fractures, particularly osteoporotic bone fractures, are common in older adults. Due to the nature of osteoporotic bone, standard methods of fracture fixation yield unsatisfactory results. Such methods cannot adequately place the broken fragments back to their pre-fracture state. For instance, with a non-osteoporotic bone fracture, common practice includes inserting rods, pins and/or screws into the bone in order to reduce the fracture and/or fix the fracture fragments to plates. Osteoporotic bone generally cannot support such a method. Another common method for non-osteoporotic bone fractures involves maintaining the bone in a cast for several weeks. Osteoporotic bone that has suffered a crush fracture, such as a Colles' fracture of the distal radius, will not heal properly if placed in a cast; the bone mechanics are altered such that the bone is shortened and/or subsides. Yet another non-osteoporotic fracture reduction method involves using an external fixation device. However, when used in elderly patients, the fixation pins may not remain within the weakened bone. Moreover, such a device typically increases the likelihood of infection at the treatment site. Further, because casts and/or an external fixation devices must be left in place for several weeks in order for the bone to heal, the lack of joint movement in the affected area often results in painful arthritis in the immobilized joints of the elderly patient.

Even where osteoporosis is not present, it is typically necessary to immobilize a fractured bone to allow the bone to properly heal. This often requires immobilization of the joints adjacent to the fractured bone—often for extended periods of time. However, such immobilization often causes the joints to degenerate over time. Often, such treatment can result in temporary or permanent loss of joint motion. At the very least, such immobilization of the joints requires extensive and often painful rehabilitation for an individual to recover the full range of their joint motion.

SUMMARY OF THE INVENTION

One aspect of the invention provides a system comprising an elongated shaft sized and configured to establish an access path to bone having an interior volume occupied, at least in part, by cancellous bone. The elongated shaft includes a generally closed distal end portion and a side opening spaced from the closed distal end. The system also includes a first tool sized and configured to be selectively inserted into the shaft and selectively removed from the shaft. The tool includes a region that, when the first tool is inserted into the shaft, is capable of being selectively aligned with and advanced through the side opening to project outside the side opening and contact cancellous bone. The system also includes a second tool sized and configured, upon removal of the first tool from the shaft, to introduce into the shaft a bone filling material for discharge through the side opening into the cancellous bone contacted by the first tool.

BRIEF DESCRIPTION OF THE DRAWINGS

FIG. 15 is a perspective view showing the obturator instrument inserted into the handle, the handle being grasped by a hand;

DETAILED DESCRIPTION OF THE PREFERRED EMBODIMENTS

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

The preferred embodiment describes improved systems and methods that embody features of the invention in the context of treating bones. This is because the new systems and methods are advantageous when used for this purpose. However, aspects of the invention can be advantageously applied for diagnostic or therapeutic purposes in other areas of the body.

The new systems and methods will be more specifically described in the context of the treatment of long bones such as the human distal radius. Of course, other human or animal bone types can be treated in the same or equivalent fashion.

I. Anatomy of the Radius

Figure 1:
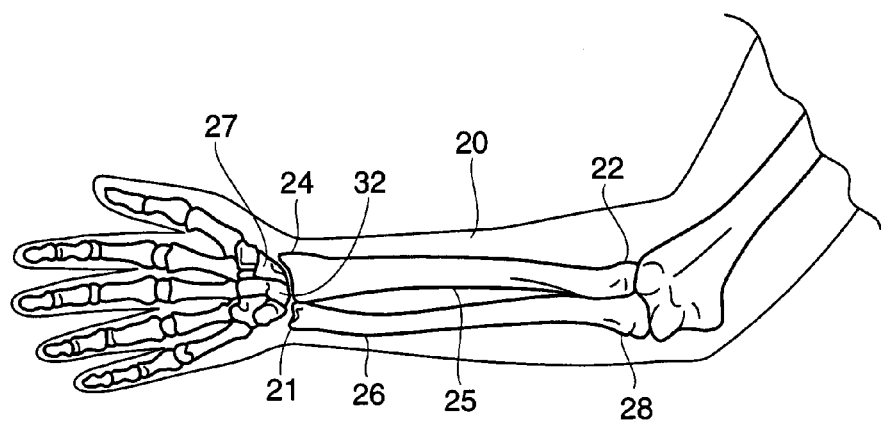
FIG. 1 is an anatomic view that shows bones of a human forearm.
Figure 2:
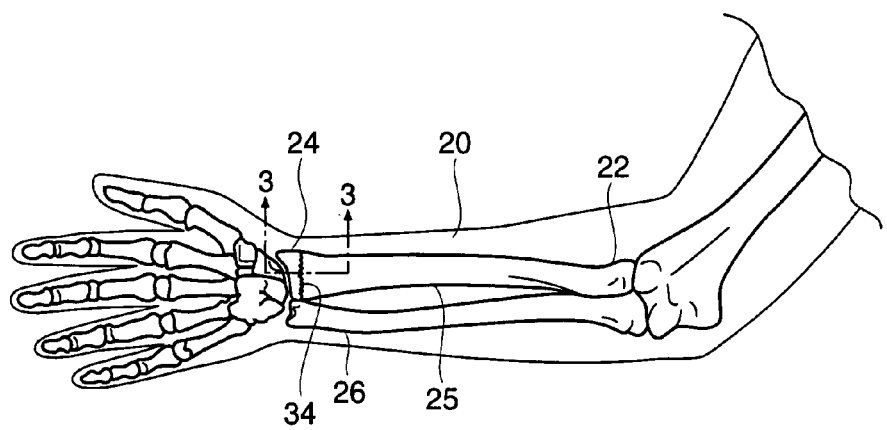
FIG. 2 is an anatomic view that shows bones of the forearm including an ulna and a fractured distal radius.

The human forearm consists of two bones, the radius and the ulna. As shown in FIGS. 1 and 2, the radius 20 is a long bone that is situated on the thumb side of the forearm, while the ulna 26 is located at the little finger side. The radius 20 lies side by side with the ulna 26, and it exceeds the ulna 26 both in length and in size.

The upper, or proximal end 22 of the radius 20 is small and articulates with a part of the elbow joint, including the proximal ulna 28. The distal end 24 of the radius 20 is large and articulates with two bones of the wrist, or carpus, known as the lunate 21 and scaphoid 27 bones. The inner, or medial side 25 of the distal radius 24 contains an ulnar notch 32 that articulates with the ulna 26.

II. Bone Fractures

The systems and methods of the present invention are especially suited for treating fractures of long bones. One type of bone fracture that may be so treated is known as a Colles' fracture or transverse wrist fracture. As shown in FIG. 2, such a fracture 34 generally occurs less than one inch from the distal end 24 of the radius 20. Colles' fractures are commonly noted in children and the elderly where the person tries to break or stop a fall by using his or her hands and arms. Colles' fractures in children are often associated with sports such as skateboarding and in-line skating. In the elderly, Colles' fractures are commonly caused by osteoporosis and/or in connection with a fall.

Figure 3:
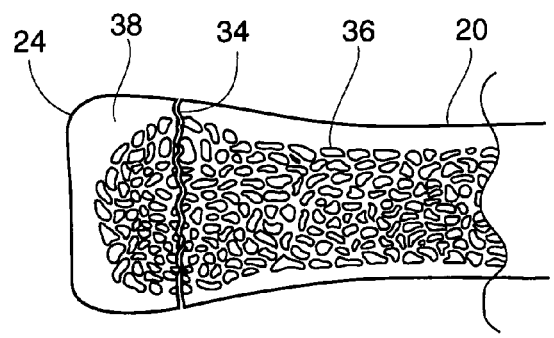
FIG. 3 is an enlarged section view of the distal radius showing cancellous bone and cortical bone in a fractured condition.

Osteoporosis is a disease of the bone that is most commonly found in the middle-aged and elderly, particularly women. It is characterized by a gradual loss of a type of bone tissue known as cancellous bone 36. As shown in FIG. 3, cancellous bone 36, also referred to as trabecular bone, is a spongy bone tissue located within the harder outer or cortical bone. Cancellous bone 36 comprises most of the bone tissue of the extremities of long bones such as the radius 20.

In contrast to cancellous bone 36, cortical bone 38 tissue is much harder and denser. Cortical bone 38 is layered over cancellous bone 36, and provides a protective layer and support for long bones such as the radius 20, as shown in FIGS. 1 and 2. At the ends of such bones, however, the cortical bone 38 layer becomes thinner. Where osteoporosis has significantly weakened the cancellous bone 36, such regions at the ends of long bones become especially prone to fracture and/or collapse.

It may be indicated, due to disease or trauma, to reduce fractured cortical bone 38 and/or compress cancellous bone 36 within long bones such as the radius 20. The compression, for example, can be used to form an interior cavity 35, which receives a filling material 99, e.g., a flowable material that sets to a hardened condition, such as poly(methylmethacrylate), as well as a medication, or combinations thereof, to provide improved interior support for cortical bone 38 or other therapeutic functions, or both. The compaction of cancellous bone 36 also exerts interior force upon cortical bone 38, making it possible to elevate or push broken and compressed bone back to or near its original pre-fracture, or other desired, condition.

III. The Instruments

Figure 4:
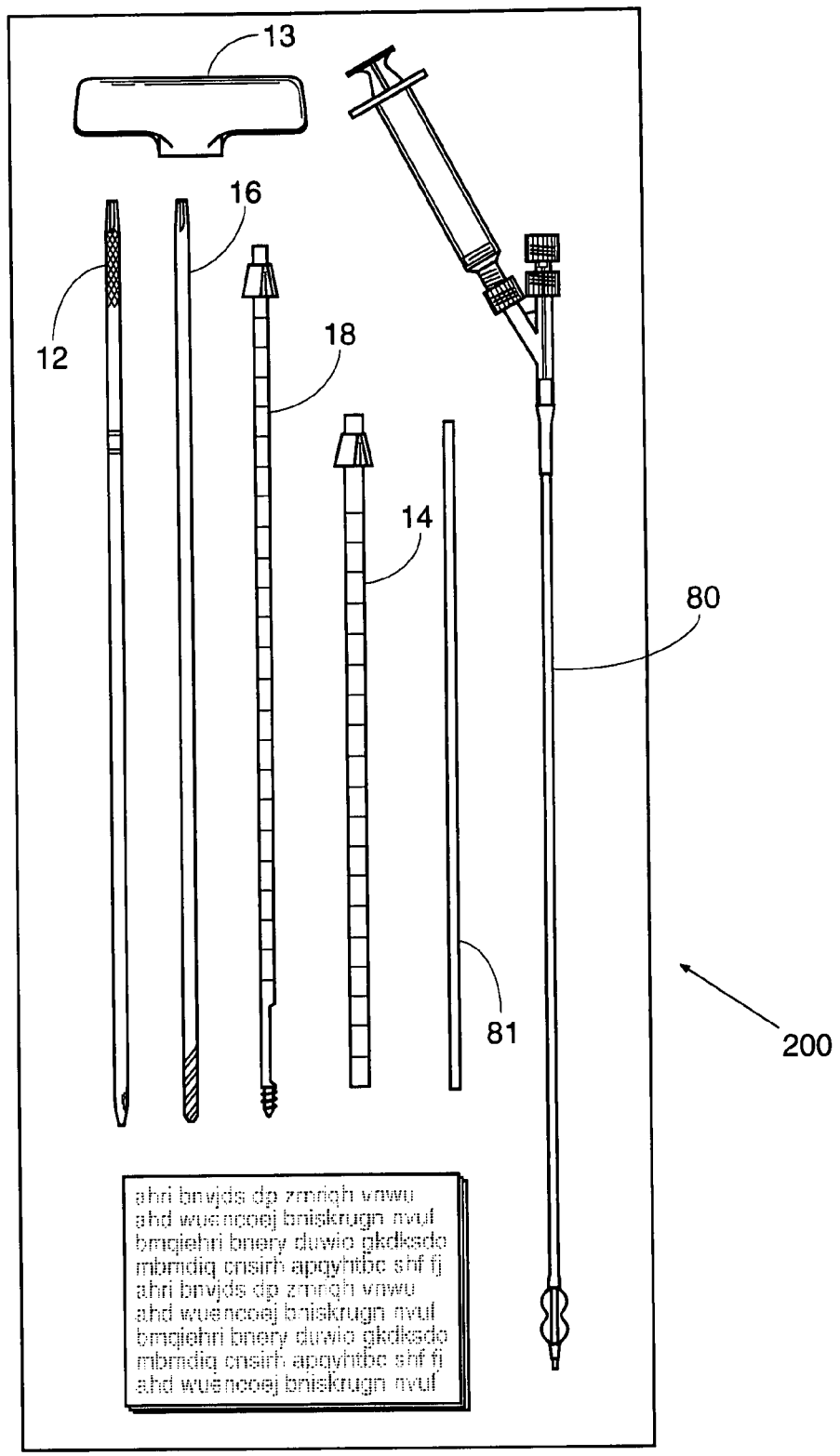
FIG. 4 is a plane view showing a kit containing a system of instruments used to treat bones and that embodies features of the invention.

FIG. 4 shows instruments, arranged as a kit 200, which are usable in association with each other to reduce fractured bone. The number and type of instruments can vary. FIG. 4 shows seven representative instruments, each having a different size and function.

In FIG. 4, the kit 200 includes an obturator instrument 12 for penetrating soft tissue and bone; a percutaneous cannula 14 that functions as a guide sheath; a drill bit instrument 16 that is used for drilling into bone; a fracture reduction cannula 18 used in reducing fractures and that is inserted into bone and designed to receive an expandable structure; a bone compaction instrument 80 that functions to deliver a filling material 99 into a cavity 35 in bone and that carries an expandable structure 86 that may be expanded in bone; a tamp 81 functions to urge residual bone filling material into bone; and a handle 13 with recesses that receives instruments 12, 14, 16 and 18.

Instruments 12, 14, 16, and 18 share some common features, although they are intended, in use, to perform different functions. Instruments 12, 14, 16, and 18 each comprise an elongated, cylindrical body 40 having a proximal end 42 and a distal end 44. Instruments 12, 14, 16, and 18 are each made of a rigid, surgical grade plastic or metal material.

A. The Obturator Instrument

Figure 5:
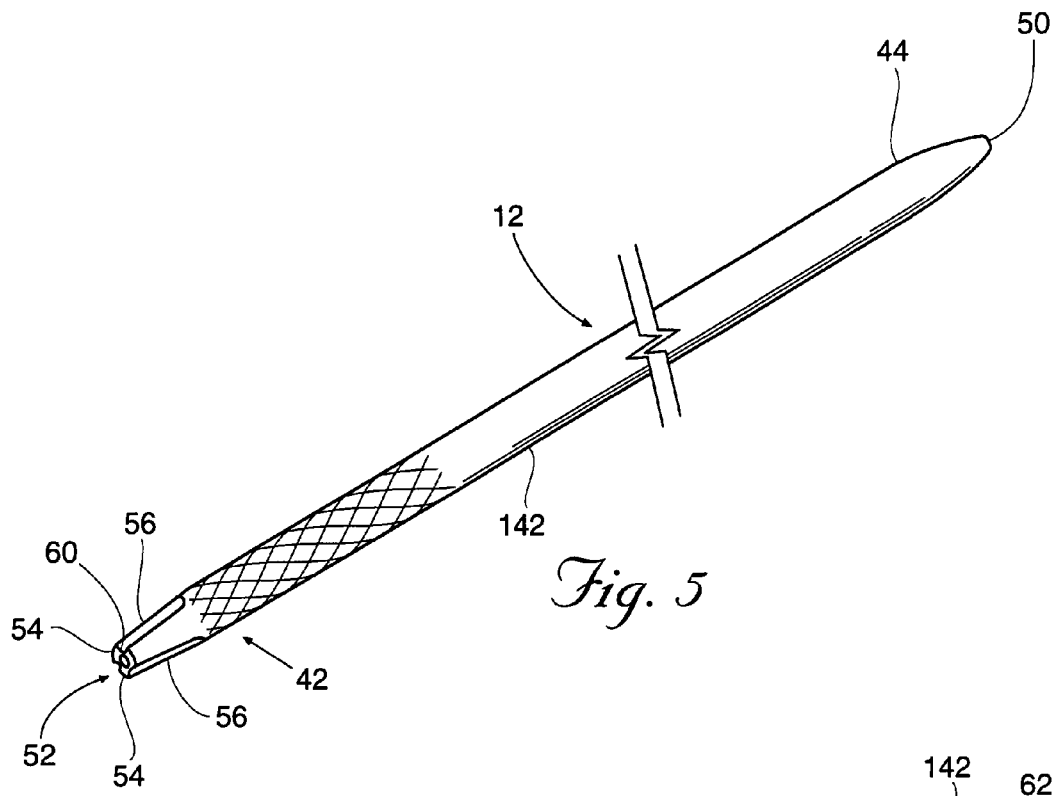
FIG. 5 is a perspective view of an obturator instrument that is contained in the kit shown in FIG. 4.

The first instrument 12 functions as an obturator. As shown in FIG. 5, its distal end 44 is tapered to present a penetrating surface 50. In use, the surface 50 is intended to penetrate soft tissue and/or bone in response to pushing or twisting forces applied by the physician at the proximal end 42. In a preferred embodiment, the proximal end 42 of the obturator instrument 12 mates with a handle 13, to be described in detail later.

The proximal end 42 of the obturator instrument 12 presents a flanged surface 52. The flanged surface 52 is designed to fit securely into a recess in the handle 13, such that pushing or twisting forces applied to the proximal end 42 of the obturator 12 instrument will not displace the obturator instrument 12. The flanged surface 52 tapers from a larger outer diameter to a smaller outer diameter in the direction of the proximal end 42. The flanged surface 52 includes an array of circumferentially spaced teeth 54 with intermediate flutes 56.

An interior bore 60 extends through the obturator instrument 12 from the distal end 44 to the proximal end 42. Desirably, the interior bore 60 is sized to accommodate a conventional surgical guide pin 108 component to aid in its deployment, as will be described in greater detail later.

The obturator instrument 12 has an outer surface 142 that is sized such that one may slide a percutaneous cannula 14 over the obturator instrument 12 as described below.

B. The Percutaneous Cannula

The second instrument 14 functions as a percutaneous cannula or guide sheath. It also serves to protect soft tissue and nerves, ligaments, muscle and vasculature from the use of a drill bit instrument 16, which will be described in greater detail later.

Figure 6:
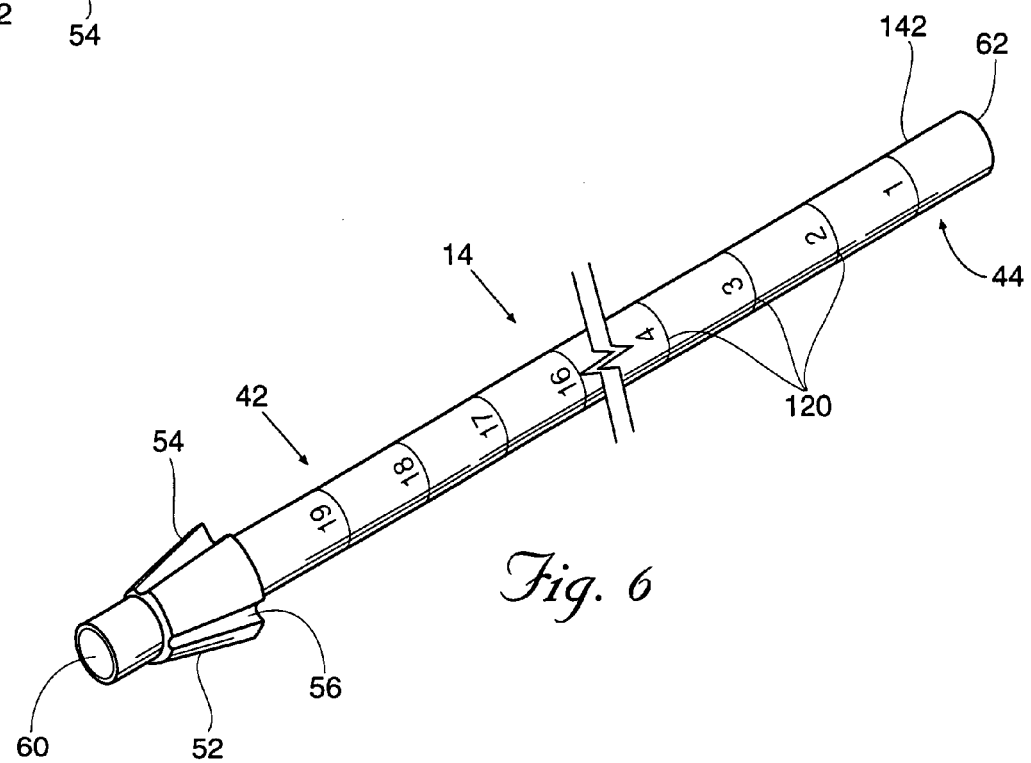
FIG. 6 is a perspective view of a percutaneous cannula that is contained in the kit shown in FIG. 4.

As shown in FIG. 6, the percutaneous cannula 14 is somewhat larger in diameter than, and is not as long as, the obturator instrument 12. In one embodiment, the cannula 14 is approximately 2 inches long, although it could be various other lengths, depending upon the thickness of the patient's soft tissue at the surgical site. Desirably, the percutaneous cannula 14 is made of metal, and contains markings 120 along its outer surface 142 to indicate the depth at which it is placed into a patient's distal radius 24.

The proximal end 42 of the percutaneous cannula 14 presents a tapered flange 52, as FIG. 6 shows. The flanged surface 52 is designed to fit securely into a recess in the handle 13, such that forces applied to the proximal end 42 of the percutaneous cannula 14 will not displace the percutaneous cannula 14. The tapered flange 52 changes from a larger diameter to a smaller diameter in the direction of the proximal end 42. The tapered flange 52 of the percutaneous cannula 14 also includes an array of circumferentially spaced teeth 54 with intermediate flutes 56. The form and orientation of the teeth 54 and flutes 56 on the percutaneous cannula 14 correspond to the form and orientation of teeth 54 and flutes 56 on the fracture reduction cannula 18.

As shown in FIG. 6, the percutaneous cannula 14 includes an interior bore 60 that extends from its distal end 44 to its proximal end 42. Desirably, the interior bore 60 is sized to accept the obturator instrument 12. The size of the interior bore 60 permits a physician to slide and rotate the percutaneous cannula 14 relative to the obturator instrument 12, and vice versa, as will be described in greater detail later.

The distal end 44 of the percutaneous cannula 14 presents an end surface 62. Desirably, the surface of the distal end 44 is designed to penetrate soft tissue. In use, the end surface 62 of the percutaneous cannula 14 is intended to penetrate soft tissue surrounding the obturator instrument 12, in response to pushing or twisting forces applied at the proximal end 42. If desired, the end surface 62 can incorporate one or more teeth (not shown) which anchor the cannula 14 to the surface of the targeted bone.

C. The Drill Bit Instrument

Figure 7:
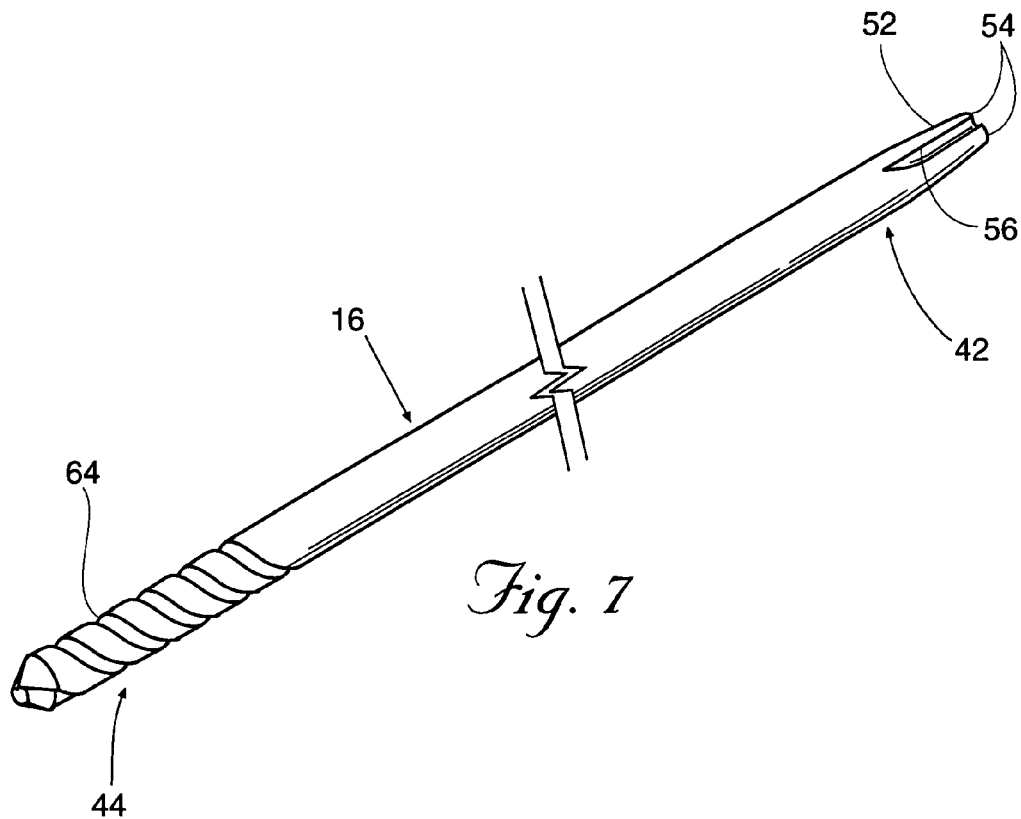
FIG. 7 is a perspective view of a drill bit instrument that is contained in the kit shown in FIG. 4.

The third instrument functions as a drill bit. As shown in FIG. 7, The drill bit instrument 16 has generally the same physical dimensions as the obturator instrument 12. Like the obturator instrument 12, the drill bit instrument 16 is intended, in use, to fit for sliding and rotational movement within the interior bore 60 of the percutaneous cannula 14.

The distal end 44 of the drill bit instrument 16 includes machined cutting edges 64, as shown in FIG. 7. In use, the cutting edges 64 are intended to penetrate hard tissue in response to rotation and longitudinal load forces applied at the proximal end 42 of the drill bit instrument 16.

As further shown in FIG. 7, the proximal end 42 presents a tapered flange 52, substantially identical to the flange 52 on the obturator instrument 12, as FIG. 5 shows. The flanged surface 52 is designed to fit securely into a recess in the handle 13, such that forces applied to the proximal end 42 of the drill bit instrument 14 will not displace the drill bit instrument 14. Like the obturator instrument 12, the tapered flange 52 changes from a larger diameter to a smaller diameter in the direction of the proximal end 42. The tapered flange 52 of the drill bit instrument 16 also includes an array of circumferentially spaced teeth 54 with intermediate flutes 56. The form and orientation of the teeth 54 and flutes 56 on the drill bit instrument 16 correspond to the form and orientation of the teeth 54 and flutes 56 on the obturator instrument 12.

D. The Fracture Reduction Cannula

Figure 8:
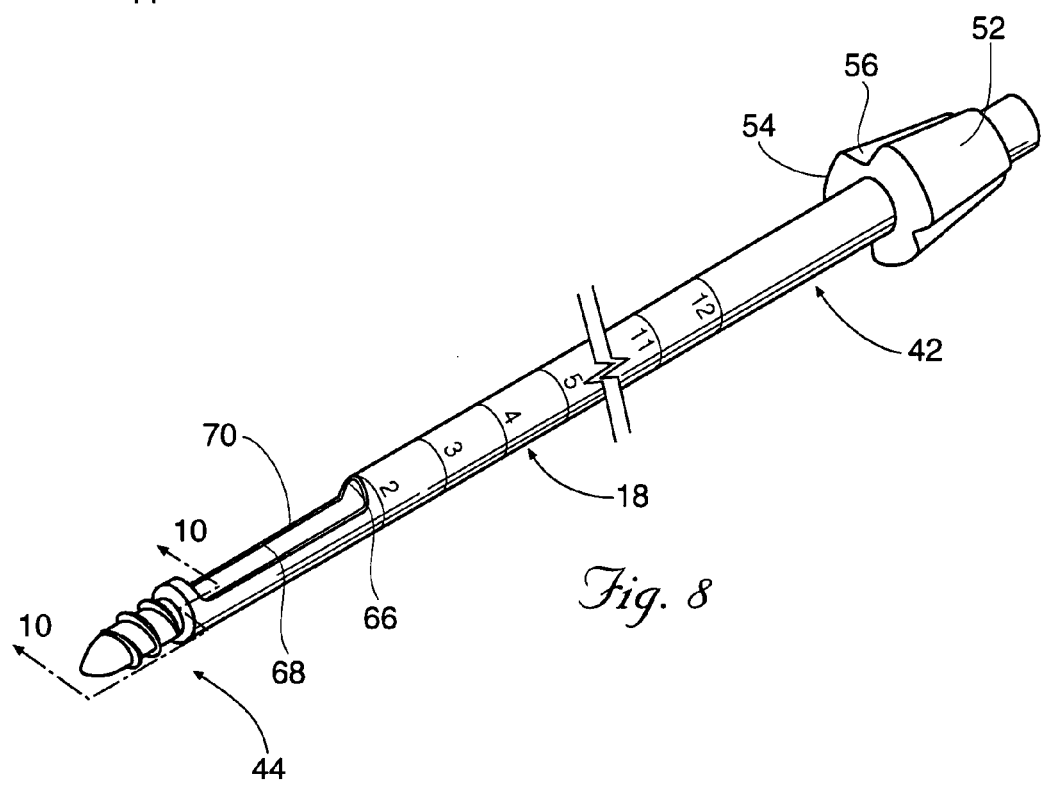
FIG. 8 is a perspective view of a fracture reduction cannula that is contained in the kit shown in FIG. 4, showing a distal end, a proximal end, and a circumferential opening.

The fourth instrument functions as a fracture reduction cannula 18. As shown in FIG. 8, the fracture reduction cannula 18 is somewhat smaller in diameter than, and is longer than, the percutaneous cannula 14. In one embodiment, the fracture reduction cannula 18 is approximately 3½ inches in length, although it could be various other lengths depending on the size of the patient and the desired location within the targeted bone. Like both the obturator instrument 12 and the drill bit instrument 16, the fracture reduction cannula 18 is intended, in use, to fit for sliding and rotational movement within the interior bore 60 of the percutaneous cannula 14.

The proximal end 42 of the fracture reduction cannula 18 presents a flanged surface 52. The flanged surface 52 is designed to fit securely into a recess in the handle 13, such that pushing or twisting forces applied to the proximal end 42 of the obturator 12 instrument will not displace the fracture reduction cannula 18. Like the percutaneous cannula 14, the flanged surface 52 of the fracture reduction cannula 18 tapers from a larger outer diameter to a smaller outer diameter in the direction of the proximal end 42. The flanged surface 52 includes an array of circumferentially spaced teeth 54 with intermediate flutes 56.

The fracture reduction cannula 18 is sized to fit within the interior bore 60 of the percutaneous cannula 14. The size of the interior bore 60 permits a physician to slide and rotate the fraction reduction cannula relative to percutaneous cannula 14, and vice versa, as will be described in greater detail later.

Figure 10A:
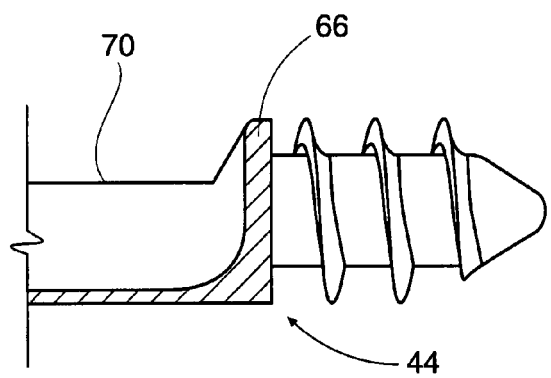
FIG. 10a is an enlarged view of the distal end of the fracture reduction cannula, the distal end being solid.
Figure 10B:
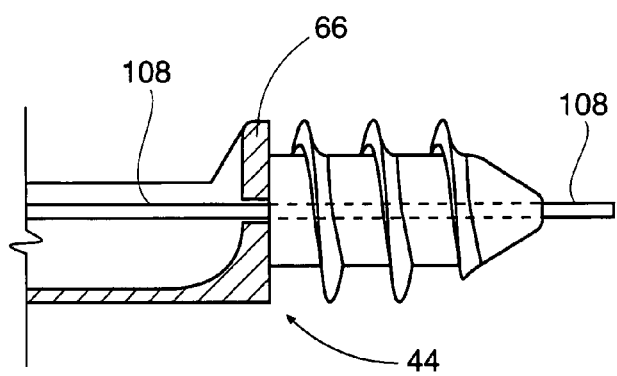
FIG. 10b is an enlarged view of the distal end of the fracture reduction cannula of FIG. 8, the distal end being open to accommodate passage of a guide pin.

As further shown in FIG. 8, the fracture reduction cannula 18 includes a side wall 66 that defines an interior bore 68 that extends from the distal end 44 of the fracture reduction cannula 18 to its proximal end 42. The interior bore 68 is adapted to allow passage of, among other things, an expandable structure 86. In a preferred embodiment, the distal end 44 of the interior bore 68 is solid, as shown in FIG. 10a. In an alternate embodiment, the distal end 44 of the bore 68 is not solid, but rather, it is open to accommodate passage of an instrument such as a guide pin 108, as shown in FIG. 10b. As another alternative, the distal end of the bore 68 could be hollow, such that a portion of the expandable structure could extend into the distal end 44 of the cannula 18.

The fracture reduction cannula 18 further includes a circumferential opening 70 in the side wall 66. In one embodiment, the circumferential opening 70 extends approximately one-half inch in length along its longitudinal axis, although the size of this opening could vary depending upon the dimensions of the targeted bone and the size of the expandable structure. The circumferential opening 70 is sized to accommodate an expandable structure 86. The circumferential opening 70 desirably also allows a filling material 99 to be placed near and/or into the fracture site.

Figure 8A:
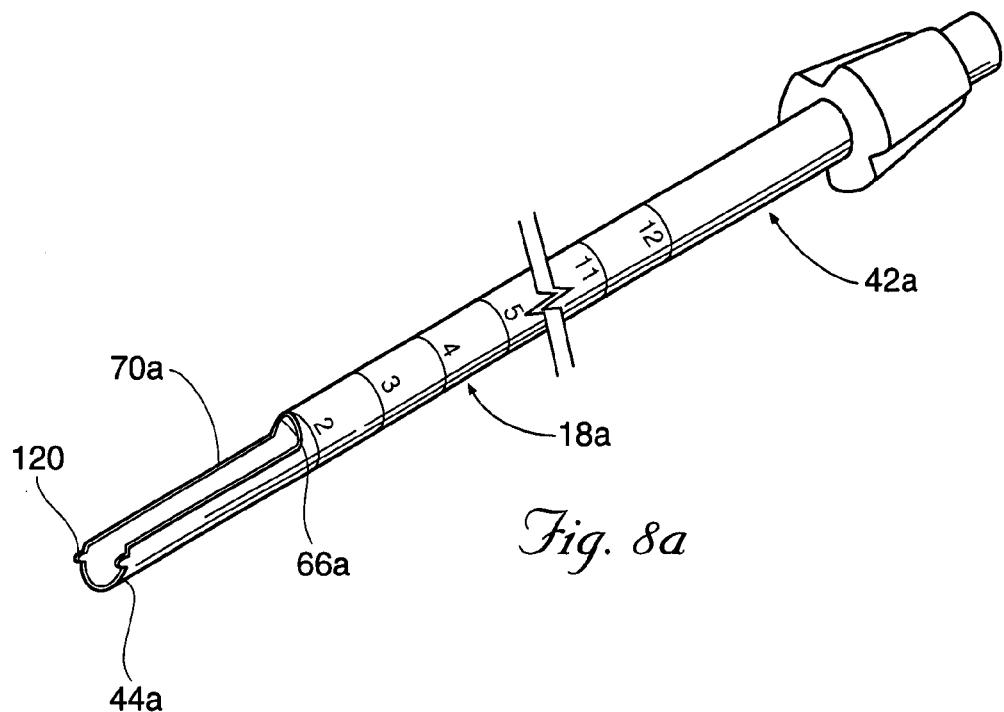
FIG. 8A is a perspective view of an alternate embodiment of a fracture reduction cannula constructed in accordance with the teachings of the present invention.

FIG. 8A depicts one alternate embodiment of a fracture reduction cannula 18A constructed in accordance with the teachings of the present invention. Because many of the disclosed components are similar to those previously described, like reference numerals will be used to denote similar components. In this embodiment, the distal end 44A of the cannula 18A is not solid, but rather extends along the side wall 66A, with one or more longitudinally extending teeth 120 disposed at the distal end 44A.

E. The Handle

Figure 14:
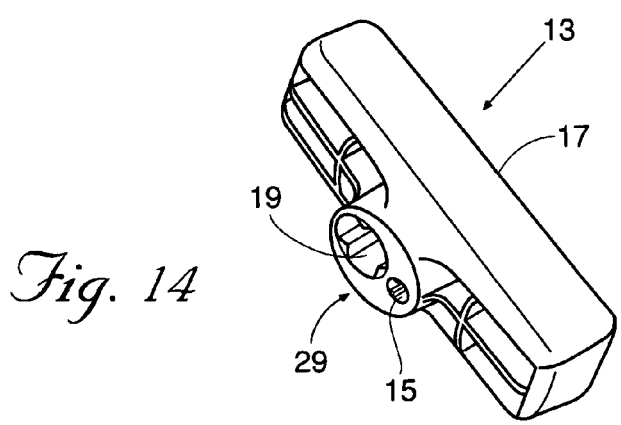
FIG. 14 is a perspective view of a handle that is contained in the kit shown in FIG. 4; showing recesses therein.

The handle 13, which can be made from a molded or cast rigid plastic or metal material, is more fully described in U.S. application Ser. No. 09/014,229, filed on Jan. 27, 1998, the disclosure of which is incorporated herein by reference. As shown in FIG. 14, the handle has a smooth upper side 17. Its lower side 29 contains recesses 15 and 19. The flanged surfaces of the obturator instrument 12, the drill bit instrument 16, the percutaneous cannula 14, and the fracture reduction cannula 18 mate with the handle 13. Recess 15 is adapted to accept the obturator 12 and the drill bit instrument 16 while recess 19 is adapted to accept the fracture reduction cannula 18. If desired, another recess can be provided (not shown) sized to accept the percutaneous cannula 14 in a similar manner.

F. The Bone Compaction and/or Displacement Instrument

Figure 11:
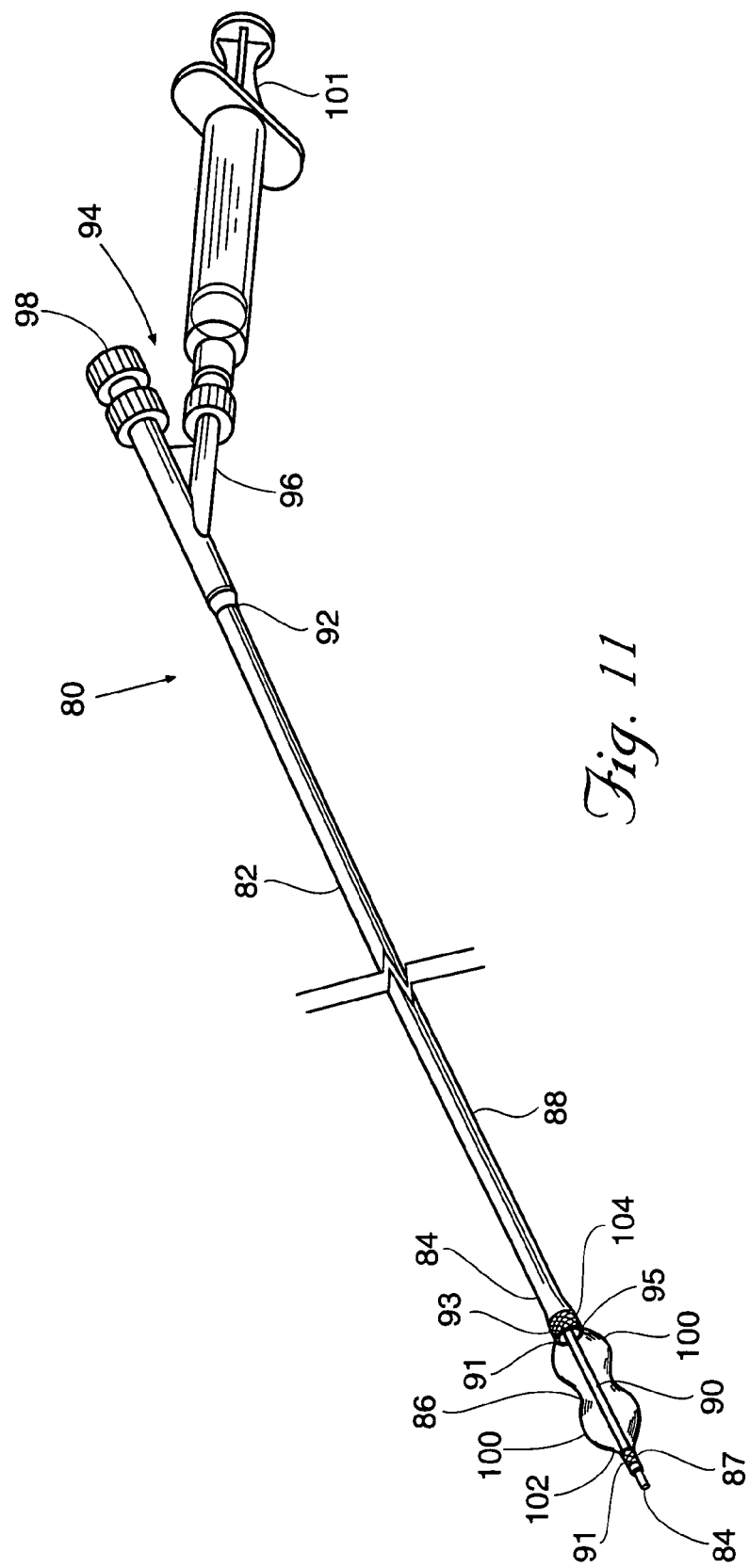
FIG. 11 is a perspective view of an instrument carrying an expandable structure, the instrument being contained in the kit shown in FIG. 4.

FIG. 11 shows an instrument 80 for accessing bone for the purpose of compacting cancellous bone 36 and/or displacing cortical bone 38. The instrument 80, and instructions for assembling same, are more fully set out in U.S. application Ser. No. 09/420,529, filed on Oct. 19, 1999, incorporated herein by reference.

Figure 20:
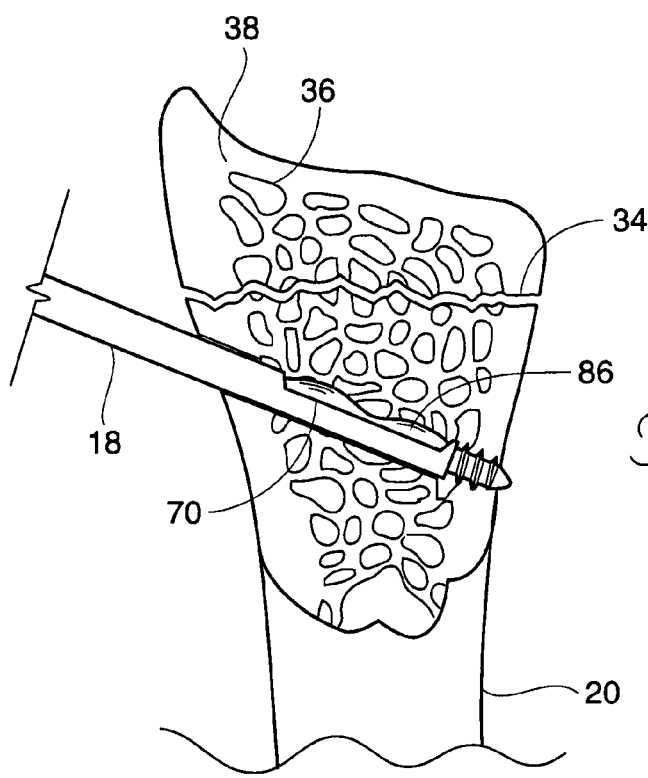
FIG. 20 is an enlarged view showing the fracture reduction cannula seated within cortical bone and containing the unexpanded expandable structure.
Figure 21:
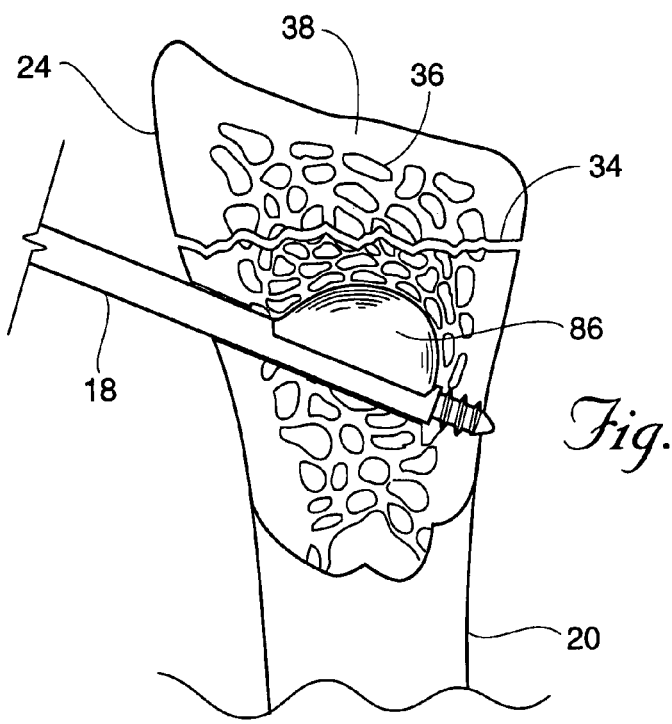
FIG. 21 is an enlarged view showing the fracture reduction cannula seated within cortical bone, containing the expanded expandable structure, and compressing cancellous bone and/or moving cortical bone.
Figure 22:
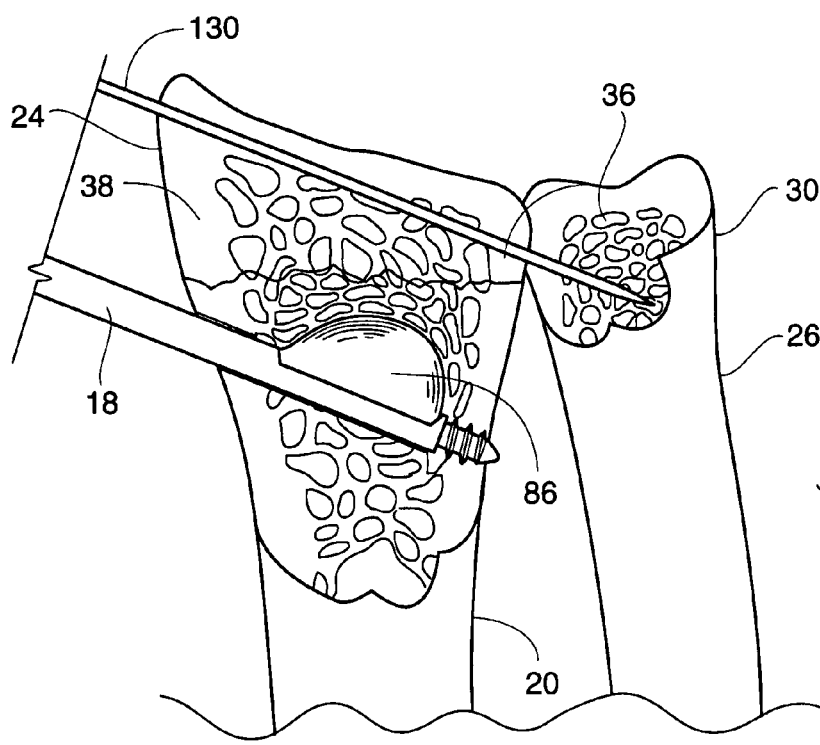
FIG. 22 is an enlarged view showing the fracture reduction cannula seated within cortical bone and containing the expanded expandable structure, showing compressed cancellous bone, displaced cortical bone, and a reduced fracture, and further showing a pin placed through the distal radius and into the ulna.

The instrument 80 includes a catheter tube assembly 82, as shown in FIG. 11. The distal end 84 of the catheter tube assembly 82 carries an expandable structure 86. In use, the expandable structure 86 is deployed and expanded inside bone, e.g., in the radius 20 as shown in FIGS. 20, 21, and 22, to compact cancellous bone 36 and/or displace cortical bone 38, as will be described later.

As further shown in FIG. 11, the instrument 80 includes an outer catheter body 88, and an inner catheter body 90 which extends through the outer catheter body 88. The proximal ends 92 of the outer 88 and inner 90 catheter bodies are coupled to a y-shaped adaptor/handle 94. The y-shaped adaptor/handle 94 carries a first port 96 and a second port 98 at its proximal end 92. The first port 96 is adapted to be coupled with an inflation syringe 101, the syringe 101 in the present case being used to deliver a pressurized liquid into the expandable structure 86. The second port 98 is adapted for insertion of a stiffening stylet (not shown) to facilitate insertion of the distal end 84 of the instrument 80.

As FIG. 11 shows, the expandable structure 86 is coupled at its proximal end 95 to the distal end 93 of the outer catheter body 88. Likewise, the expandable structure 86 is coupled at its distal end 87 to the distal end 84 of the inner catheter body 90.

The outer catheter body 88 defines an interior bore, through which the inner catheter body 90 extends. The interior bore, in use, conveys a pressurized liquid, e.g., a radio-opaque solution such as CONRAY® solution, or another fluid into the expandable structure 86 to expand it.

The material from which the expandable structure 86 is made should possess various physical and mechanical properties to optimize its functional capabilities to compact cancellous bone 36, and to move cortical bone 38. Desirably, the expandable structure 86 has the capability to move cortical bone 38 from a fractured condition to a pre-fractured or other desired condition, or both. The three most important properties of expandable structure 86 are the ability to expand its volume; the ability to deform in a desired way when expanding and assume a desired shape inside bone; and the ability to withstand abrasion, tearing, and puncture when in contact with cancellous bone 36.

The desired properties for the structure material, and the description for creating a pre-formed structure, are more fully set out in U.S. application Ser. No. 09/420,529, filed on Oct. 19, 1999.

As shown in FIG. 11, the expandable structure 86 carries radio-opaque markers 91 located at a distal end 102 and at a proximal end 104 of segmented shaped regions 100 of the expandable structure 86. The radio opaque markers 91 function to indicate, under fluoroscopic or other real-time monitoring, the location of the segmented shaped regions 100 in relation to the circumferential opening 70 of the fracture reduction cannula 18.

Figure 12:
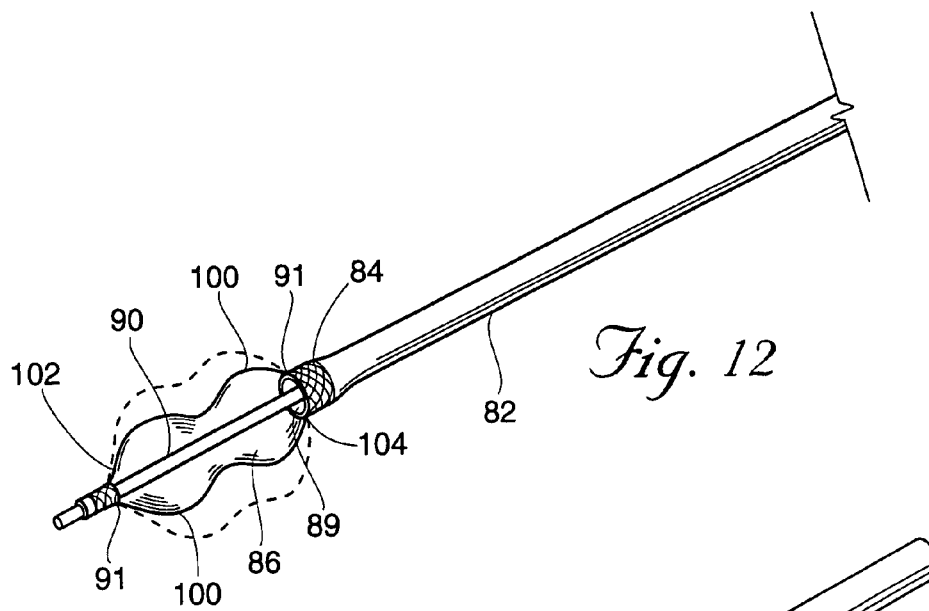
FIG. 12 is an enlarged perspective view of an instrument, showing the expandable structure in an unexpanded state and, in broken lines, the expandable structure in an expanded state.

FIG. 12 illustrates the expandable structure in a collapsed state (solid lines) and an expanded state (broken lines).

G. The Pin

One or more conventional smooth Steinman pins 130 or Kirschner ("K") wires may be provided to assist in aligning and/or stabilizing fracture fragments, as will be described in greater detail later.

H. The Filling Material Instruments

Figure 13:
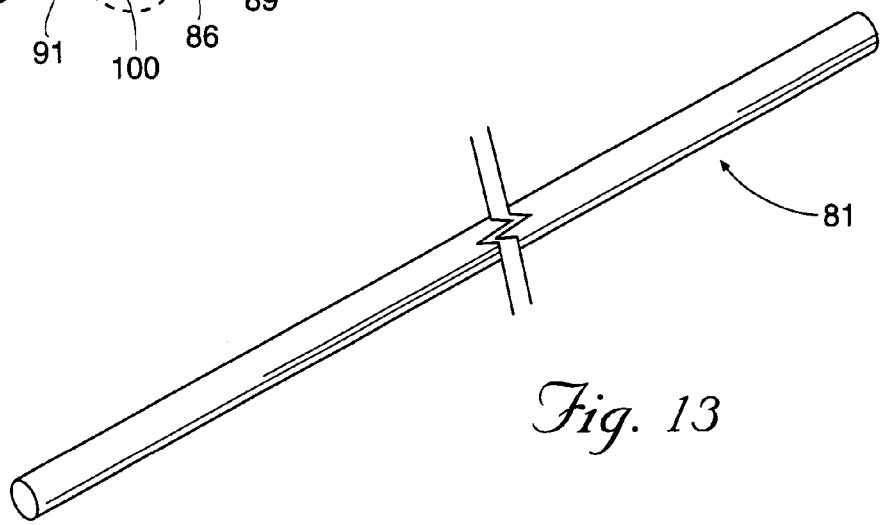
FIG. 13 is a perspective view of a tamp that is contained in the kit shown in FIG. 4.

The filling material 99 instruments include a tamp 81 as shown in FIG. 13, and a standard syringe. The filling material 99 is introduced through the syringe and into the fracture reduction cannula 18. Residual filling material 99 may be urged through the fracture reduction cannula 18 by employing the tamp 81, as will be described in greater detail later.

I. The Kit

As shown in FIG. 4, a kit 200 is provided, including instruments 12, 13, 14, 16, 18, 80, and 81. The kit 200 and the instruments contained therein are sterile and are sealed until an instance of use.

IV. Illustrative Use of the System

The size and shape of the access tools and/or expandable structure(s) 86 to be used, and the amount of bone to be moved, are desirably selected by the physician, taking into account the morphology and geometry of the site to be treated. The shape of the joint, the bones and soft tissues involved, and the local structures that could be harmed if moved inappropriately, are generally understood by medical professionals using textbooks of human anatomy along with their knowledge of the site and its disease and/or injury. The physician is also desirably able to select the desired shape and size of the expandable structure 86, the cavity 35 and their placement based upon prior analysis of the morphology of the targeted bone and joint using, for example, plain film x-ray, fluoroscopic x-ray, or MRI or CT scanning. The shape, size and placement are desirably selected to optimize the strength and ultimate bonding of the fracture relative to the surrounding bone and/or tissue of the joint.

In a typical procedure, a patient is placed under local anesthesia, although general anesthesia may instead be employed. Where a fracture 34 is that of a distal radius 24, a physician makes an incision of approximately one (1) centimeter on the radial aspect of the distal radius 24. In an alternate embodiment, one may access the distal radius 24 by an approach through the ulna 26. The distance between the incision and the fracture 34 is approximately 0.5 centimeter. Of course, while the present procedure is described in the context of a minimally invasive surgery, various other surgical approaches, including percutaneous, subcutaneous, non-open, partially open and/or completely open surgical approaches may be utilized in accordance with the teachings of the present invention.

After making the incision, the physician spreads the soft tissue by using a small clamp designed to avoid injury to nearby nerves, muscles, and vasculature. The physician then acquires the obturator instrument 12 and the handle 13. The obturator instrument 12 may have at its proximal end 42 a flanged surface 52 that mates with a recess 15 within the handle 13. Use of the handle 13 with the obturator instrument 12 will produce axial as well as radial movement, as shown in U.S. application Ser. No. 09/014,229, filed on Jan. 27, 1998. The physician then fits the proximal end 42 of the obturator instrument 12 into recess 15 in the handle 13, as shown in FIG. 15.

Figure 15A:
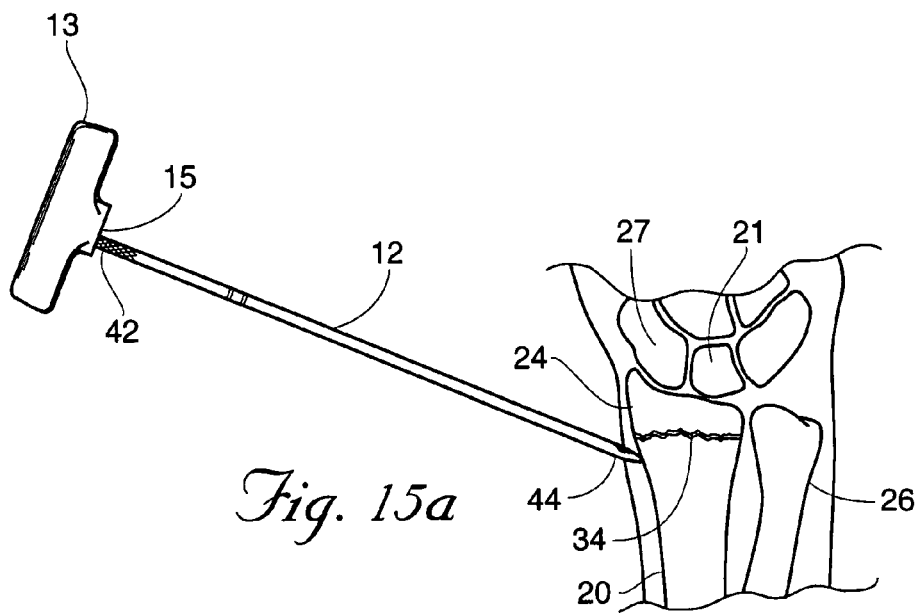
FIG. 15a is a side section view showing the obturator instrument inserted into the handle and advanced to the distal radius.

The physician next twists the handle 13 while applying longitudinal force to the handle 13. In response, the tapered surface of the obturator instrument 12 rotates and penetrates soft tissue through the incision, as shown in FIG. 15a. The physician may also tap the handle 13, or otherwise apply appropriate additional longitudinal force to the handle 13, to advance the obturator instrument 12 through soft tissue.

Under fluoroscopic monitoring or other real-time monitoring, the physician advances the obturator instrument 12 through soft tissue down to the distal radius 24, as FIG. 15a shows. The obturator instrument 12 is inserted distal to proximal from the radial side of the radius 20 to the ulnar side of the radius 20. The obturator instrument 12 is introduced into the radius 20. Desirably, the obturator instrument 12 is introduced at an angle between minus 10 degrees and 45 degrees to the radio-carpal joint. More desirably, the obturator instrument 12 is introduced at an angle between zero degrees and 30 degrees to the radio-carpal joint. Most desirably, the obturator instrument 12 is introduced at an angle equal to the angle of the radio-carpal joint, i.e., approximately 23 degrees. Of course, if desired, the physician may utilize various other approach paths to access the bone, including a dorsal approach.

Figure 16:
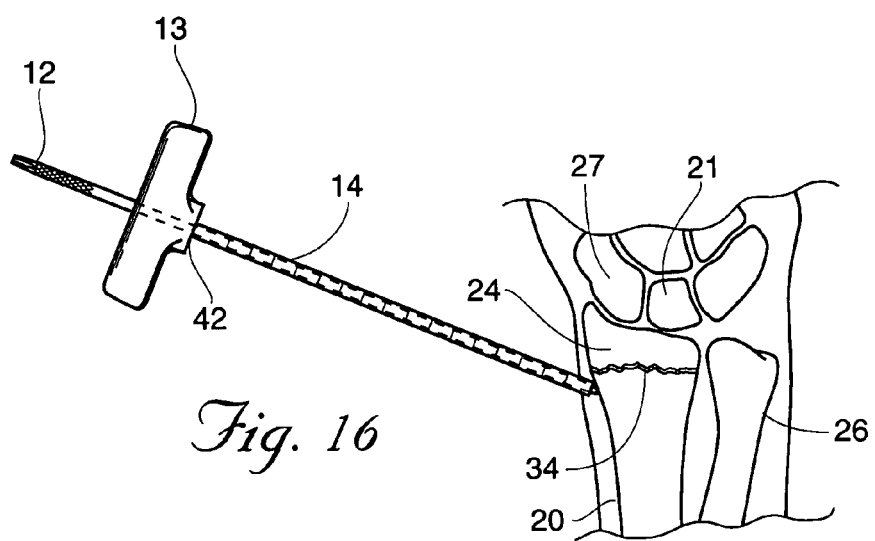
FIG. 16 is a side section view showing the percutaneous cannula inserted over the obturator instrument and advanced to the distal radius.

The physician next removes the handle 13 from the obturator instrument 12 and places the proximal end 42 of the percutaneous cannula 14 in a recess 19 in the handle 13. The physician slides the percutaneous cannula 14 over the obturator instrument 12, distal end 44 first. The physician then twists the handle 13 while applying longitudinal force to the handle 13, in order to seat the percutaneous cannula 14 against and/or into the external cortical bone 38, as shown in FIG. 16. Once the percutaneous cannula 14 is seated in the cortical bone 38, the obturator instrument 12 is removed, proximal end 42 first.

Figure 28:
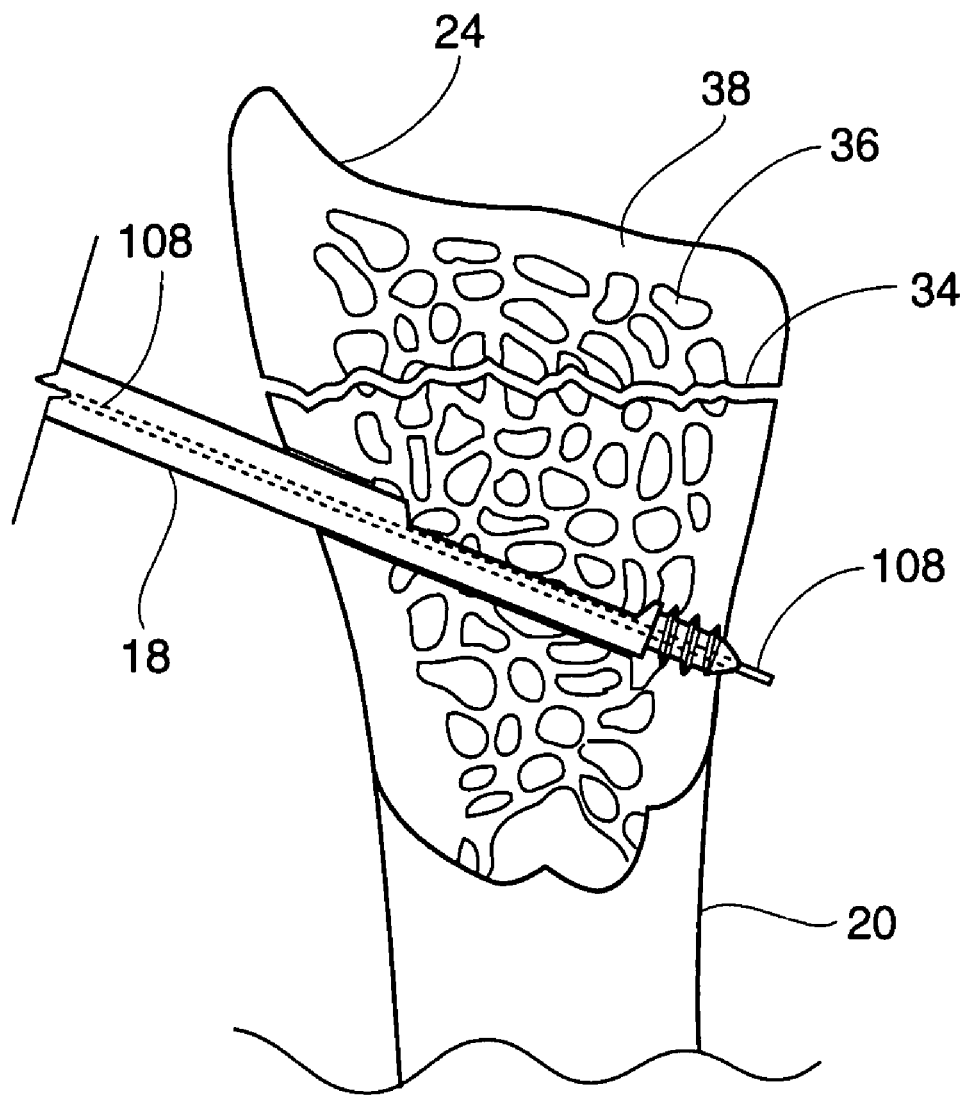
FIG. 28 is an enlarged view showing an alternate embodiment of the fracture reduction cannula with a guide pin placed therethrough.

In an alternate embodiment, instead of using the obturator instrument 12 to access external cortical bone 38, the physician may instead insert a conventional spinal needle, the needle having an outer sheath and a stylus, into the bone. Upon puncturing the bone, the physician removes the stylus and inserts a guide pin 108 through the outer sheath. The sheath is then removed and the fracture reduction cannula 18 is deployed over the guide pin 108. The physician then fits the proximal end 42 of the percutaneous cannula 14 into a recess 19 in the handle 13 and slides the assembly, distal end 44 first, over the fracture reduction cannula 18, as shown in FIG. 28. Subsequently, the guide pin 108 is removed, proximal end first.

Figure 17:
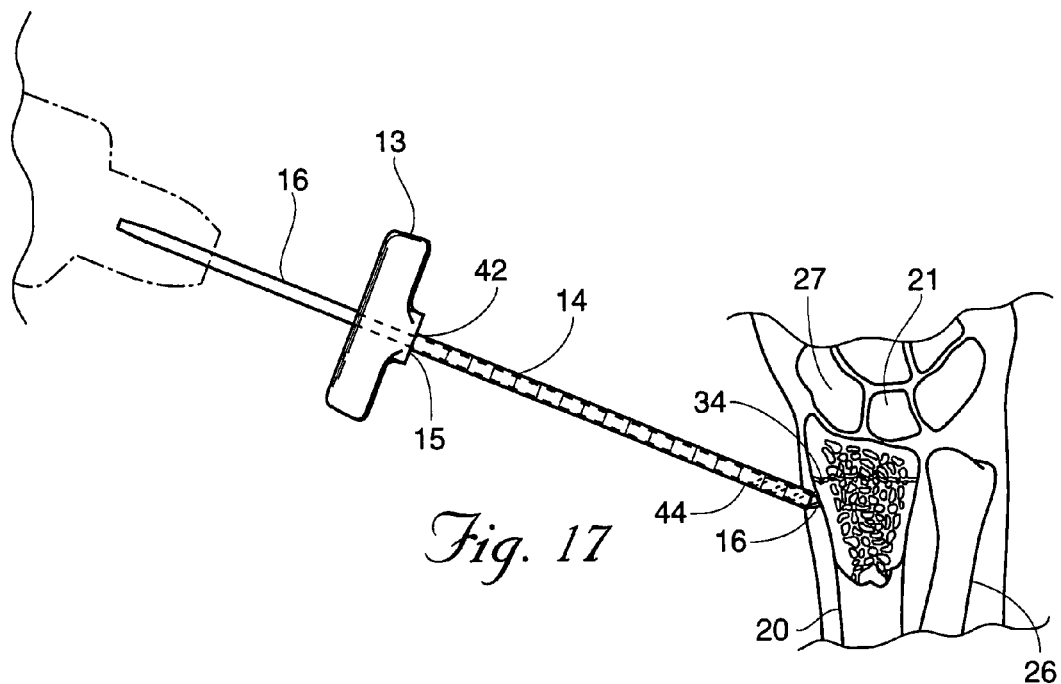
FIG. 17 is a side section view showing the drill bit instrument within the percutaneous cannula and advanced to the distal radius, and further showing the distal radius fracture and cancellous bone.

After removing the obturator instrument 12, or the guide pin 108 as in the case of the alternate embodiment described above, the handle 13 is removed from the percutaneous cannula 14. As shown in FIG. 15, the proximal end 42 of a drill bit instrument 16 is then placed in a recess in the handle 13. The preferred size of the drill bit 16 is 3.2 millimeters. The physician slides the drill bit assembly distal end 44 first through the bore 60 of the percutaneous cannula 14. Using manual pressure, the drill bit instrument 16 is advanced down to and into the distal radius 24. As an alternate embodiment, instead of using manual pressure, the physician could connect the proximal end 42 of the drill bit instrument 16 to a conventional motor-driven drill. The physician directs the drill bit instrument 16 to penetrate the cortical bone 38 and the cancellous bone 36 of the distal radius 24, as shown in FIG. 17.

Figure 8B:
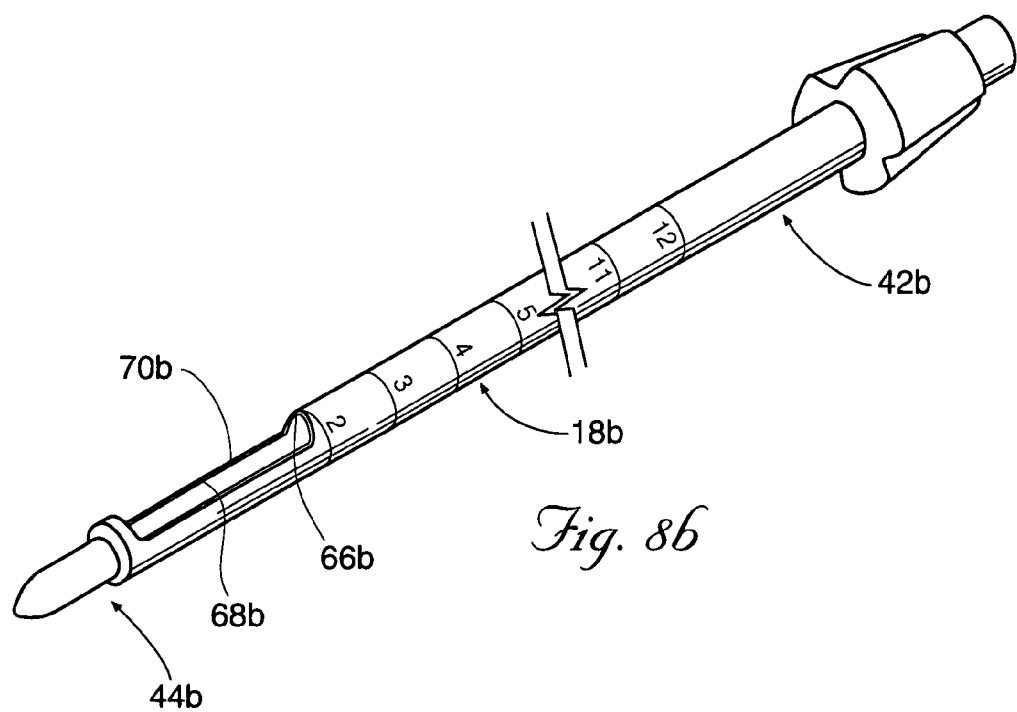
FIG. 8B is a perspective view of another alternate embodiment of a fracture reduction cannula constructed in accordance with the teachings of the present invention.
Figure 9:
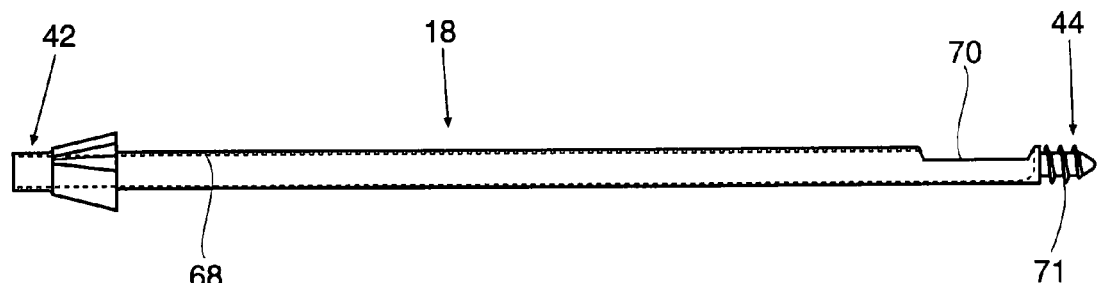
FIG. 9 is a side view of the fracture reduction cannula of FIG. 8 showing an end interior bore therethrough.
Figure 18:
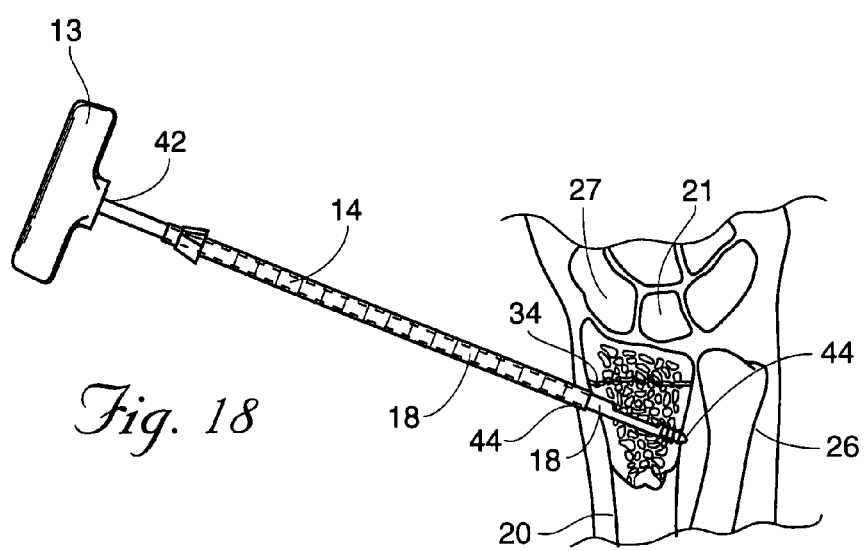
FIG. 18 is a side section view showing the fracture reduction cannula within the percutaneous cannula and advanced into the cancellous bone of the distal radius, and further showing the circumferential opening facing the fracture.
Figure 19:
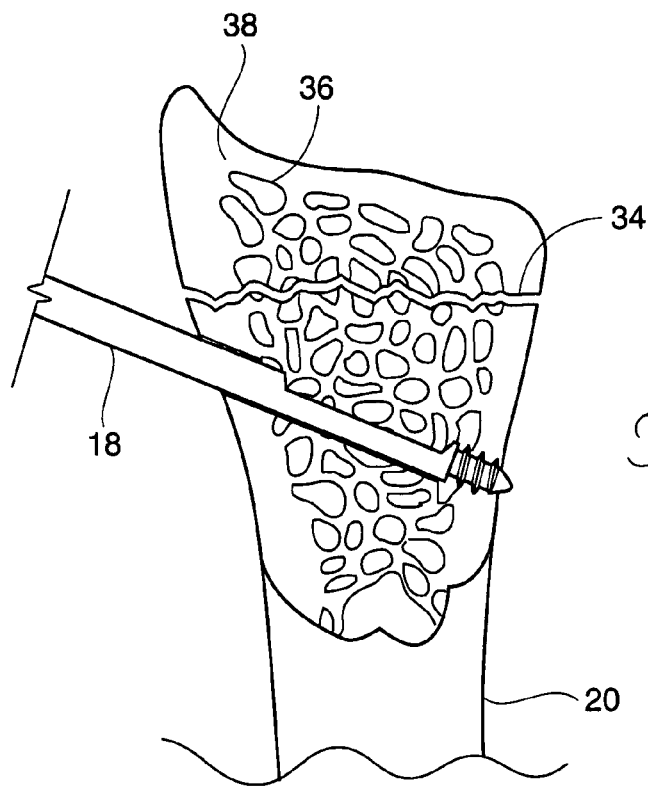
FIG. 19 is an enlarged view showing the fracture reduction cannula seated within cortical bone.

After drilling through cortical bone 38 and into cancellous bone 36, the physician removes the drill bit instrument 16 from the handle 13. The fracture reduction cannula 18 is then inserted, distal end 44 first, into the bore of the percutaneous cannula 14, as shown in FIG. 18. The distal end 44 of the fracture reduction cannula 18 extends beyond the distal end 44 of the percutaneous cannula 14. In an alternate embodiment, the physician may at this point remove the percutaneous cannula 14, leaving only the fracture reduction cannula 18 in place. In one embodiment, it is preferred to employ a fracture reduction cannula 18 that has screw threads 71 on its distal end 44 as shown in FIG. 9, thereby enabling the fracture reduction cannula 18 to be anchored to an interior surface of cortical bone 38 in response to rotation of the fracture reduction cannula 18, e.g., by using the handle 13. In an alternative embodiment (see FIG. 8B), the physician may employ a fracture reduction cannula 18 that has a blunt, tapered distal end 44 instead of screw threads 71 on the distal end 44. If such a fracture reduction cannula 18 is employed, the physician may choose to drill a hole in cortical bone 38 in which to seat the blunt, tapered distal end 44. Desirably, if the distal end 44 is blunt and tapered, the fracture reduction cannula 18 may be adapted to rotate independently from the distal end 44. As another alternative, a cannula 18A as depicted in FIG. 8A could be inserted into the targeted bone as previously described, with the teeth 120 anchoring the distal end 44A of the cannula 18A to the cortical wall (not shown) of the targeted bone region. With this embodiment, it would not be necessary to drill a hole through the cortical wall to anchor the distal end 44*a* of the cannula 18A.

In another embodiment, the access path can be made directly through the one or more fracture lines in the targeted bone. Such an arrangement minimizes trauma to the fractured bone (by reducing additional damage to healthier sections of the bone) and permits the creation of a cavity 35 which extends to each side of the fracture line.

The fracture reduction cannula 18 is placed into the cancellous bone 36 of the distal radius 24 such that the circumferential opening 70 is facing towards the fracture, as shown in FIG. 18. The fracture reduction cannula 18 is checked radiologically to ensure that the circumferential opening 70 is contained entirely within the cancellous bone 38 of the radius 20. In one embodiment, one or more markings (not shown) can be provided on the proximal end 42 of the cannula 18, allowing the physician to visually gauge the orientation of the cannula 18. In one embodiment, the fracture reduction cannula 18 is approximately 3 to 4 inches in length.

The physician can now acquire the catheter tube assembly 82 for placement into the bore 68 of the fracture reduction cannula 18. In one embodiment, the uninflated expandable structure 86 carried by the catheter tube measures 12 millimeters in length from its proximal end to its distal end, although structures 86 of varying lengths could be used, including expandable structures 86 of 15 mm or 20 mm, depending upon the size of the patient, the size and location of the fracture 34, the size of the opening 70 and the cavity 35 size and shape and/or displacement of bone desired. The catheter tube assembly 82 is now introduced into the bore 68 of the fracture reduction cannula 18.

The physician guides the catheter tube assembly 82 through the fracture reduction cannula 18 until the expandable structure 86 enters and lies adjacent to the circumferential opening 70 of the fracture reduction cannula 18, as shown in FIG. 20. In one embodiment, the distal end 44 of the fracture reduction cannula 18 is solid, as shown in FIG. 9, thus preventing an expandable structure 86 from emerging from the distal end 44 of the fracture reduction cannula 18. The placement of the expandable structure 86 within the circumferential opening 70 can be determined by radio opaque markers 91 located on the expandable structure 86, as shown in FIG. 11. The expandable structure 86 is passed into bone through the fracture reduction cannula 18 in a normally collapsed and non-inflated condition. The expandable structure 86 is now aligned with cancellous bone 36.

Figure 24:
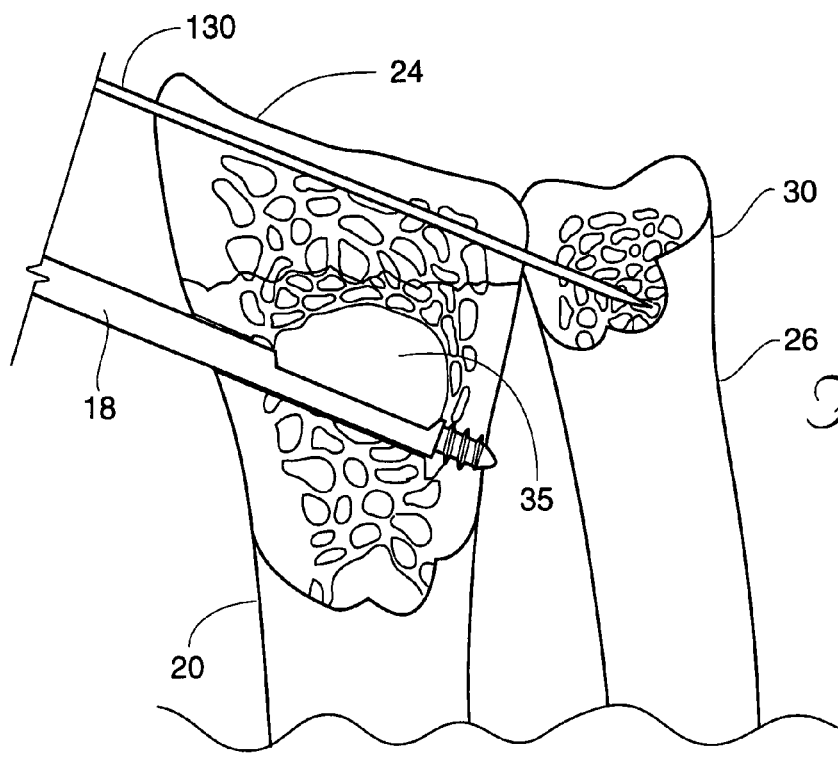
FIG. 24 is an enlarged view showing a cavity created by expansion of the expandable structure in the distal radius, the pin in place, the fracture reduction cannula, and the cavity ready to receive a bone filling material.
Figure 25:
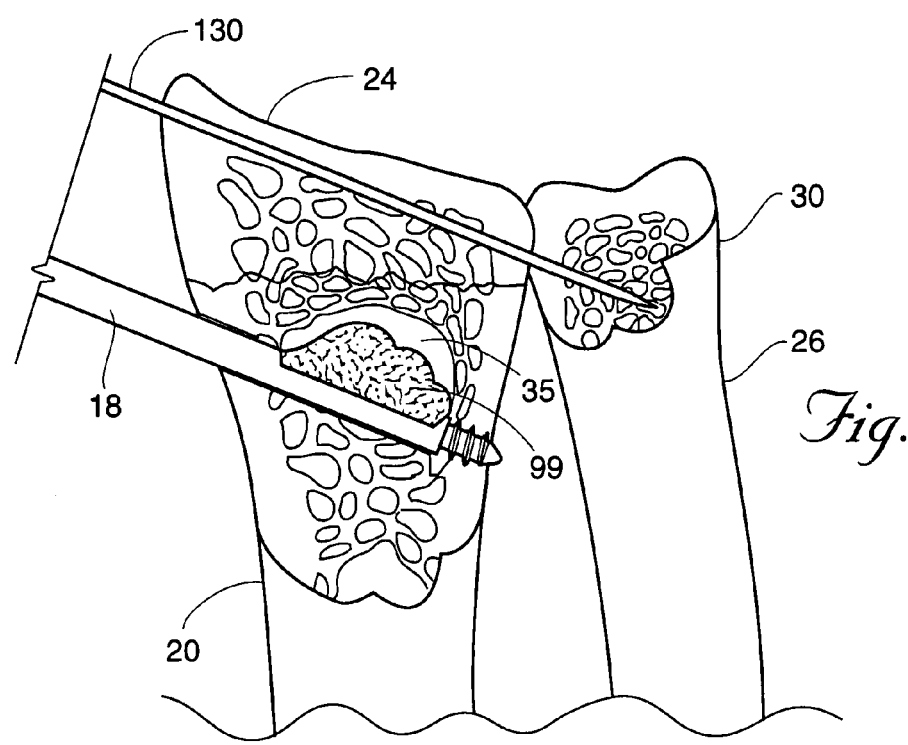
FIG. 25 is an enlarged view showing the filling material beginning to fill the cavity.

The physician, after verifying that the expandable structure 86 is adjacent the circumferential opening 70, conveys a pressurized fluid, such as a radio opaque fluid, through the catheter tube assembly 82 and into the expandable structure 86. The expandable structure 86 now expands into cancellous bone 36, as shown in FIG. 21. The fracture reduction cannula 18 desirably directs the expanding structure 86 towards the fracture 34. Progress of the expandable structure 86 is evaluated both on A-P, or anterior-posterior, and lateral x-rays. Preferably, the A-P x-ray is used until the distal end 24 of the radius 20 begins to move, at which point both A-P and lateral views are obtained. The pressurized fluid is used to inflate the expandable structure 86 and expand it through the circumferential opening 70 in order to compress cancellous bone 36 and/or displace cortical bone 38. The expandable structure 86 will desirably form an interior cavity 35 in the cancellous bone 36, as shown in FIG. 24. Desirably, the compressed cancellous bone 36 will seal any fractures 34 and/or cracks in the targeted bone through which the filling material 99, to be described later, can flow out of the targeted treatment area.

The compression of cancellous bone 36, as shown in FIG. 22, can also exert an interior force upon the surrounding cortical bone 38. The interior force will elevate or push broken and compressed bone back to or near its original pre-fracture, or other desired, condition. Once the fracture 34 is well aligned, it is preferred to introduce one or more smooth "Steinman" pins 130 or K-wires proximal to the joint surface of the radius 20 and distal to the inflated expandable structure 86. The pins 130 can be placed across the distal end 24 of the radius 20 and into the distal ulna 30, as shown in FIGS. 22 and 24-27. Alternatively, the pin(s) 130 can be secured into the radius 20 without penetrating the ulna 26. The pin 130 desirably prevents the fracture 34 from displacing upon further manipulation of the wrist and/or contraction of the expandable structure 86. If desired, additional pins 130 can be used to manipulate and/or secure other cortical bone fragments, or can be used to further secure a single bone fragment.

In one or more alternate embodiments, the pins 130 can be introduced once a bone fragment has been displaced to a prior position, but prior to completion of the inflation steps. For example, where inflation of the balloon displaces a fragment to a desired position, but addition cavity creation is desired, the fragment may be secured in position using one or more pins 130, and then the balloon can be further inflated to create a larger cavity 35 and/or compress additional cancellous bone 36.

Figure 23:
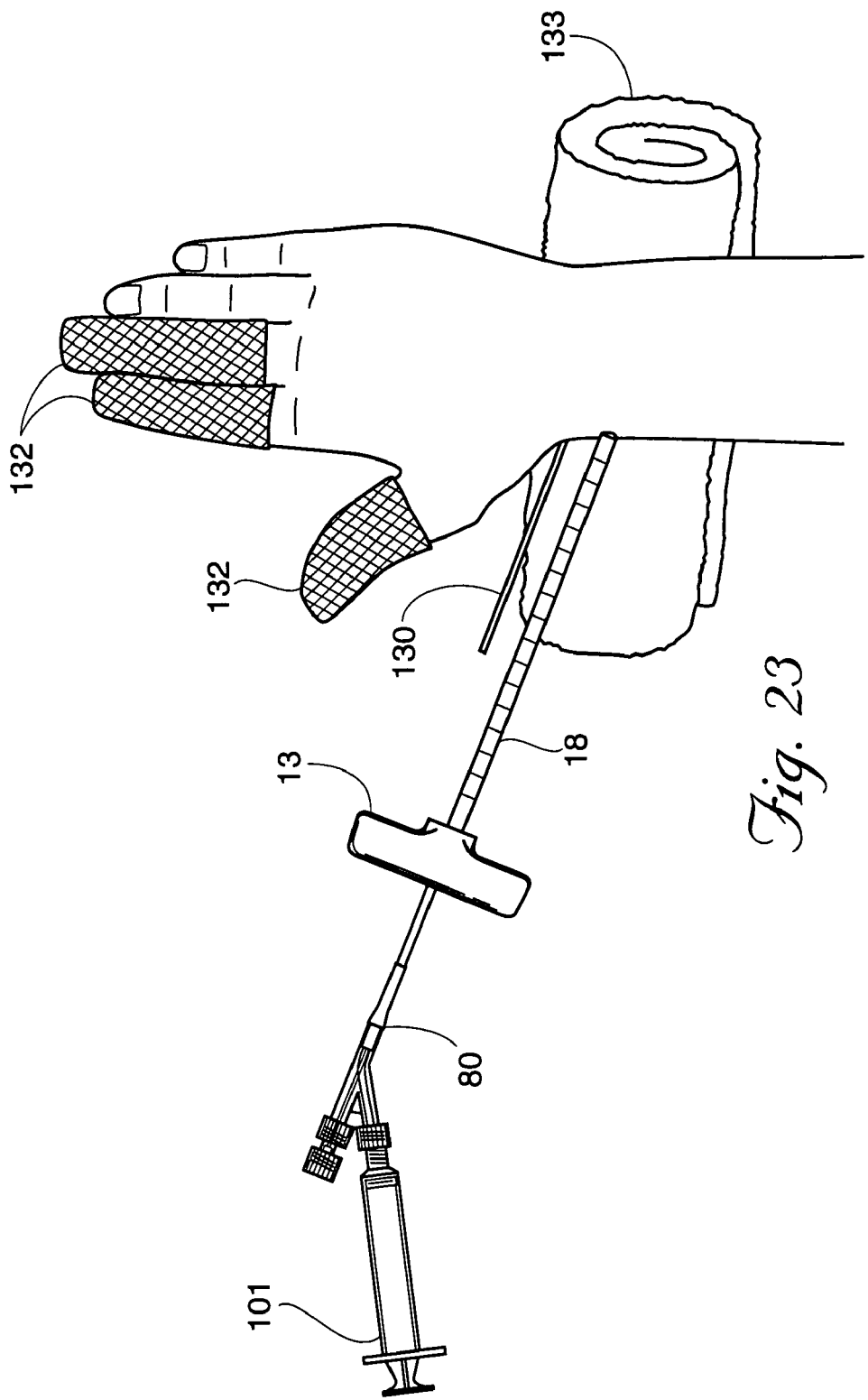
FIG. 23 is a top view showing a patient's forearm on a rolled towel, with horizontal finger traps on the patient's fingers, the instrument inserted through the handle and into the percutaneous cannula, with the fraction reduction cannula hidden from view, and the pin inserted into the patient's wrist.

As shown in FIG. 23, in one preferred embodiment, the patient's fingers of the affected arm can be placed in horizontal finger traps 132, with the patient's palm facing the treatment table. A rolled towel 133 may be placed under the patient's wrist. By grasping the finger traps 132 and gently pulling on them, the physician can extend the patient's arm and thus reduce any pressure that may be exerted at the fracture site. This approach potentially allows for an improved correction of the volar tilt (15 degrees) of the distal radius 24. If desired, this can be accomplished prior to, during or after fracture reduction has been accomplished.

Figure 27:
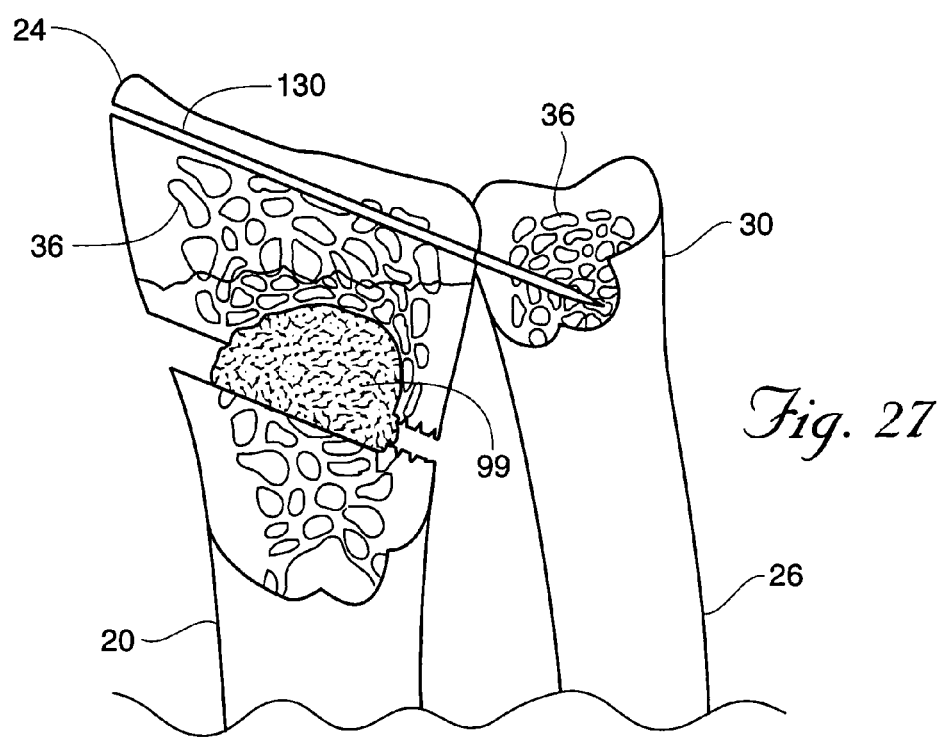
FIG. 27 is an enlarged view showing the filled cavity with the fracture reduction cannula and tamp removed.

Once the interior cavity 35 is formed and any desired pins 130 set in place, the expandable structure 86 is collapsed and the catheter tube assembly 82, with the collapsed expandable structure 86, is removed. As shown in FIG. 27, the cavity 35 is now in a condition to receive a filling material 99 through the fracture reduction cannula 18. The filling material 99 can be any of a number of available bone filling materials, which include, but are not limited to, resorbable and/or remodelable bone cements, calcium phosphates, allograft tissue, autograft tissue, poly(methylmethacrylate) or Norian SRS☐ bone matrix. The filling material may be introduced into the fracture reduction cannula by means of a syringe (not shown). The filling material 99 progresses through the fracture reduction cannula 18 and into the circumferential opening 70 of the fracture reduction cannula 18. The filling material 99 desirably provides improved interior structural support for cortical bone 38. Desirably, the filling material 99 extends proximal to any cortical defects created by the drill bit instrument 16 and by the fracture reduction cannula 18. In one embodiment, approximately two (2) to seven (7) cubic centimeters of filling material 99 can be injected into the cavity 35.

Figure 26:
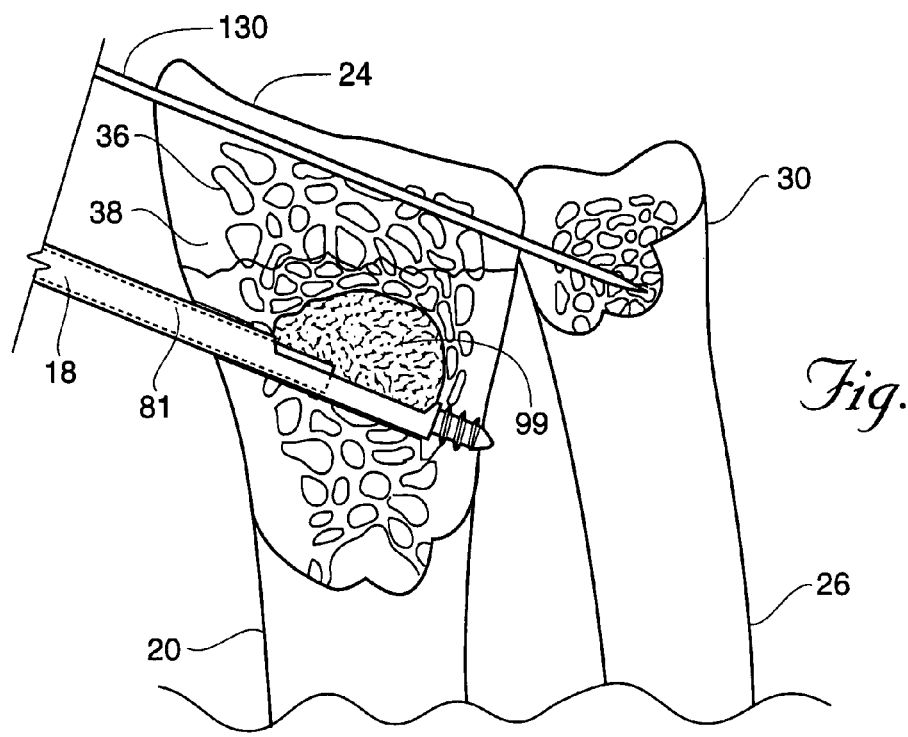
FIG. 26 is an enlarged view showing the tamp urging the filling material fully into the cavity.

After the filling material 99 is introduced, a tamp 81 may be inserted into the fracture reduction cannula 18 as shown in FIG. 26, for the purpose of urging residual filling material 99 into the interior cavity 35. Tamping of the filling material 99 may also cause the material to interdigitate into the surrounding cancellous bone 36, further supporting the cancellous 36 and cortical bone 38. The fracture reduction cannula 18 and (if still present) the percutaneous cannula 14 are removed. If desired, any void remaining subsequent to removal of the cannula 18 can be filled with filling material 99. The patient should be kept immobile for ten to fifteen minutes. After the immobilization, the pin(s) 130 and finger traps 132 can be removed and the hand of the patient is checked for motion. The entry site is covered with appropriate antibiotics and an adhesive strip is applied.

Figure 21A:
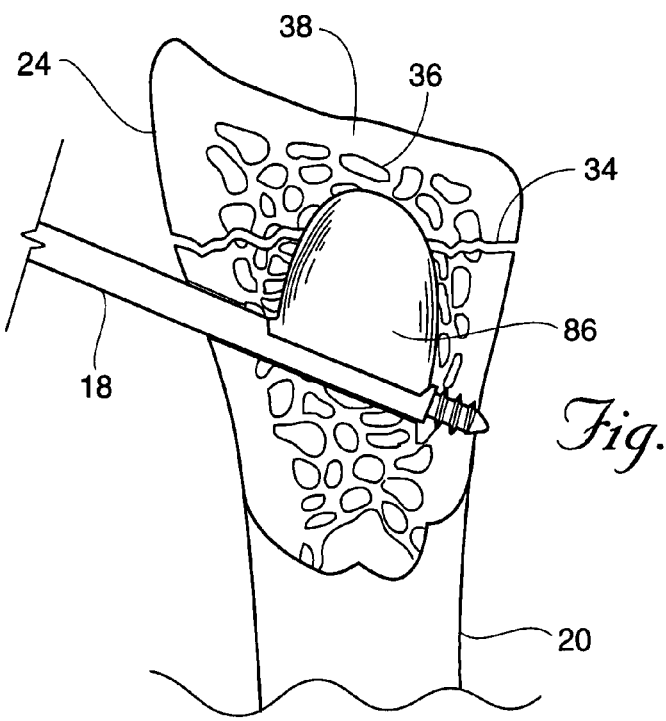
FIG. 21A is an enlarged view showing a fracture reduction cannula seated within cortical bone, with the expanded expandable structure compressing cancellous bone and/or moving cortical bone and creating a cavity which extends across a fracture line in the targeted bone.
Figure 22A:
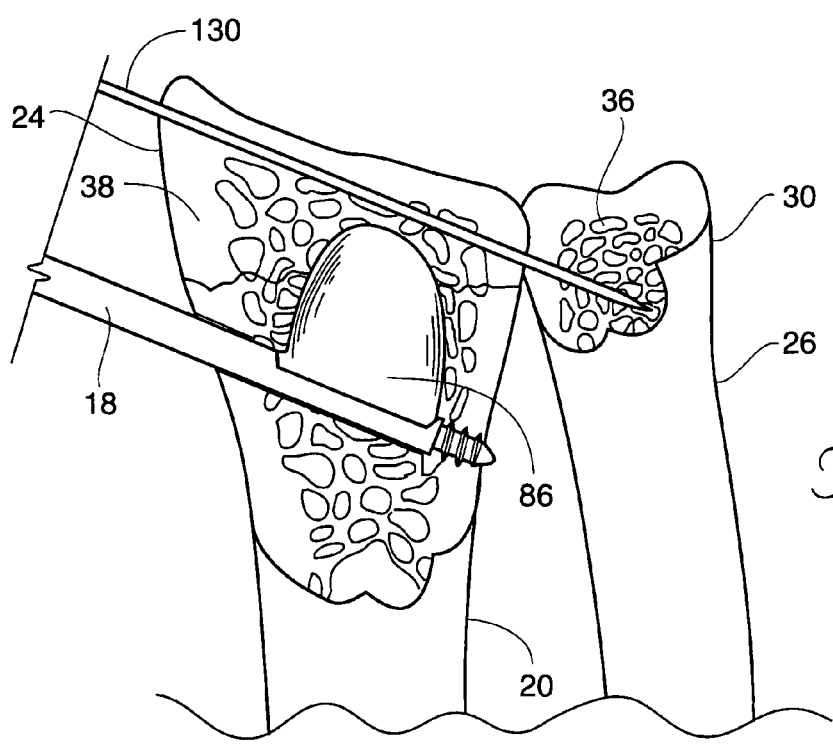
FIG. 22A is an enlarged view showing a fracture reduction cannula seated within cortical bone and containing the expanded expandable structure, showing compressed cancellous bone, displaced cortical bone, a reduced fracture, and a cavity extending across a fracture line in the cortical bone, and further showing a pin placed through the distal radius and into the ulna.

FIGS. 21A and 22A depict an alternate embodiment in which the expandable structure 86 is expanded within the fractured bone to create a cavity 35 which extends across at least one fracture line in the bone. In this embodiment, the filling material 99 ultimately introduced into the cavity 35 can extend across the fracture line and desirably interdigitate into the cancellous bone of the fragmented section(s). This will desirably anchor the fractured sections to the bone, thereby permitting the bone to undergo significant distractive and/or torsional loading without slippage along the fracture line(s) and/or subsequent re-fracture of the treated bone.

If desired, the disclosed systems and methods could be used with equal utility in reducing and/or reinforcing fractures in bones of younger individuals and/or individuals not having osteoporosis. In such patients, the present systems and methods would allow for an immediate resumption of activity, reducing the opportunity for degradation of adjacent joints and promoting healing of the fracture.

The features of the invention are set forth in the following claims.

We claim:

1. A system comprising an elongated shaft sized and configured to establish an access path to bone having an interior volume occupied, at least in part, by cancellous bone, the elongated shaft including a closed distal end portion terminating in a distal tip, and a side opening spaced from the closed distal end portion and the distal tip, the elongated shaft further including a bone engaging structure, located distally of the side opening, the bone engaging structure comprising threads extending between the distal tip and the side opening to anchor the distal end of the elongated shaft in the interior volume of the bone, a first tool sized and configured to be selectively inserted into the shaft and selectively removed from the shaft, the first tool including a region that is capable of being selectively aligned with and advanced through the side opening to project outside the side opening and contact cancellous bone, when the first tool is selectively inserted into the shaft, and a second tool sized and configured, upon removal of the first tool from the shaft, to introduce into the shaft a bone filling material for discharge through the side opening into the cancellous bone.

2. A system according to claim 1 wherein contact between the region and the cancellous bone modifies cancellous bone for introduction of bone filling material.

3. A system according to claim 1 wherein the bone filling material comprises bone cement.

4. A system according to claim 1 wherein the region of the first tool includes a curved surface sized to project from the side opening.

5. A system according to claim 1 wherein the region of the first tool forms into a curved surface during advancement of the region through the side opening.

6. A system according to claim 1 wherein the region advances through the side opening by expansion.

7. A system according to claim 1 wherein the region comprises an inflatable body that advances through the side opening by expansion.

8. A system according to claim 1 wherein contact between the region and cancellous bone creates a cavity in cancellous bone.

9. A system according to claim 1 wherein the elongated shaft and the first tool are sized and configured to be mutually manipulated as a unit within cancellous bone.

10. A system according to claim 1 wherein the shaft comprises a cannula.

11. A system according to claim 1 further comprising a percutaneous cannula sized for receipt of the elongated shaft.

* * * * *